(12) United States Patent
Hossack et al.

(10) Patent No.: US 6,201,900 B1
(45) Date of Patent: Mar. 13, 2001

(54) MULTIPLE ULTRASOUND IMAGE REGISTRATION SYSTEM, METHOD AND TRANSDUCER

(75) Inventors: John A. Hossack, Palo Alto; John W. Sliwa, Jr., Los Altos; Samuel H. Maslak, Woodside; Edward A. Gardner, San Jose; Gregory L. Holley, Mountain View; David J. Napolitano, Menlo Park, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/340,542

(22) Filed: Jun. 28, 1999

Related U.S. Application Data

(60) Division of application No. 08/916,585, filed on Aug. 22, 1997, now Pat. No. 6,014,473, which is a continuation-in-part of application No. 08/621,561, filed on Mar. 25, 1996, now abandoned, which is a continuation-in-part of application No. 60/012,578, filed on Feb. 29, 1996.

(51) Int. Cl.$^7$ .............................. G06K 9/00; G06K 9/32; H04N 7/01; H04N 7/08; A61B 8/00

(52) U.S. Cl. .................... 382/294; 382/131; 382/236; 382/276; 348/441; 348/473; 600/437; 600/443; 600/444

(58) Field of Search .................................. 382/236, 248, 382/276, 294, 295, 298, 300, 131; 348/473, 441, 469; 600/437, 444, 443

(56) References Cited

U.S. PATENT DOCUMENTS

| | | | |
|---|---|---|---|
| Re. 30,397 | 9/1980 | King | 600/443 |
| 4,841,977 | 6/1989 | Griffith et al. | 600/439 |
| 4,917,097 | 4/1990 | Proudian et al. | 600/463 |
| 4,947,852 | 8/1990 | Nassi et al. | 600/465 |
| 5,000,185 | 3/1991 | Yock | 600/459 |

(List continued on next page.)

FOREIGN PATENT DOCUMENTS

| | | |
|---|---|---|
| 0 357 164 | 10/1991 | (EP) . |
| 077352 A1 | 5/1997 | (EP) . |
| WO 97/00482 | 1/1997 | (WO) . |
| WO 98/25509 | 6/1998 | (WO) . |

OTHER PUBLICATIONS

"B&K 8558 transducer and B&K 8557 transducer", B&K Medical product brochure, (date unknown), 1 page.

(List continued on next page.)

*Primary Examiner*—Phuoc Tran
*Assistant Examiner*—Daniel G. Mariam
(74) *Attorney, Agent, or Firm*—Brinks Hofer Gilson & Lione

(57) ABSTRACT

An ultrasonic imaging system includes an ultrasonic transducer having an image data array and a tracking array at each end of the image data array. The tracking arrays are oriented transversely to the image data array. Images from the image data array are used to reconstruct a three-dimensional representation of the target. The relative movement between respective frames of the image data is automatically estimated by a motion estimator, based on frames of data from the tracking arrays. As the transducer is rotated about the azimuthal axis of the image data array, features of the target remain within the image planes of the tracking arrays. Movements of these features in the image planes of the tracking arrays are used to estimate motion as required for the three-dimensional reconstruction. Similar techniques estimate motion within the plane of an image to create an extended field of view.

9 Claims, 20 Drawing Sheets

U.S. PATENT DOCUMENTS

| | | | |
|---|---|---|---|
| 5,070,879 | 12/1991 | Herres | 600/444 |
| 5,081,993 | 1/1992 | Kitney et al. | 600/455 |
| 5,107,837 * | 4/1992 | Ophir et al. | 600/437 |
| 5,107,844 | 4/1992 | Kami et al. | 600/463 |
| 5,161,535 * | 11/1992 | Short et al. | 600/437 |
| 5,161,537 | 11/1992 | Hashimoto et al. | 600/463 |
| 5,186,176 | 2/1993 | Hiki et al. | 600/447 |
| 5,186,177 | 2/1993 | O'Donnell et al. | 600/463 |
| 5,199,437 | 4/1993 | Langberg | 600/463 |
| 5,211,176 | 5/1993 | Ishiguro et al. | 600/463 |
| 5,257,629 | 11/1993 | Kitney et al. | 600/463 |
| 5,273,045 | 12/1993 | Chihara et al. | 600/463 |
| 5,305,104 * | 4/1994 | Jensen et al. | 348/473 |
| 5,320,105 | 6/1994 | Bonnefous et al. | 600/454 |
| 5,325,860 | 7/1994 | Seward et al. | 600/468 |
| 5,327,895 | 7/1994 | Hashimoto et al. | 600/459 |
| 5,345,940 | 9/1994 | Seward et al. | 600/463 |
| 5,368,037 | 11/1994 | Eberle et al. | 600/463 |
| 5,377,682 | 1/1995 | Ueno et al. | 600/446 |
| 5,379,642 | 1/1995 | Reckwerdt et al. | 73/625 |
| 5,380,411 | 1/1995 | Schlief | 204/157 |
| 5,381,067 | 1/1995 | Greenstein et al. | 310/334 |
| 5,384,594 | 1/1995 | Sieber et al. | 348/169 |
| 5,386,830 | 2/1995 | Powers et al. | 600/455 |
| 5,396,285 | 3/1995 | Hedberg et al. | 348/163 |
| 5,398,691 | 3/1995 | Martin et al. | 128/660.06 |
| 5,402,793 | 4/1995 | Gruner et al. | 128/660.1 |
| 5,409,688 | 4/1995 | Quay | 424/9.52 |
| 5,410,205 | 4/1995 | Gururaja | 310/328 |
| 5,410,516 | 4/1995 | Uhlendorf et al. | 367/7 |
| 5,417,213 | 5/1995 | Prince | 600/413 |
| 5,417,214 | 5/1995 | Roberts et al. | 600/413 |
| 5,425,366 | 6/1995 | Reinhardt et al. | 600/458 |
| 5,433,207 | 7/1995 | Pretlow, III | 600/458 |
| 5,435,311 | 7/1995 | Umemura et al. | 600/439 |
| 5,438,554 | 8/1995 | Seyed-Bolorforosh et al. | 367/140 |
| 5,443,071 | 8/1995 | Banjamin et al. | 600/455 |
| 5,456,255 | 10/1995 | Abe et al. | 600/443 |
| 5,456,257 | 10/1995 | Johnson et al. | 600/458 |
| 5,456,259 | 10/1995 | Barlow et al. | 600/459 |
| 5,464,851 | 11/1995 | Lipschultz | 514/373 |
| 5,469,849 | 11/1995 | Sasaki et al. | 600/443 |
| 5,471,988 | 12/1995 | Fujio et al. | 600/439 |
| 5,471,990 | 12/1995 | Thirsk | 600/455 |
| 5,474,073 | 12/1995 | Schwartz et al. | 128/661.1 |
| 5,479,926 | 1/1996 | Ustuner et al. | 600/440 |
| 5,482,046 | 1/1996 | Deitrich | 600/458 |
| 5,487,388 | 1/1996 | Rello et al. | 128/660.09 |
| 5,492,125 | 2/1996 | Kim et al. | 600/443 |
| 5,497,776 | 3/1996 | Yamazaki et al. | 600/445 |
| 5,503,153 | 4/1996 | Liu et al. | 600/454 |
| 5,515,853 | 5/1996 | Smith et al. | 600/437 |
| 5,517,537 | 5/1996 | Greene et al. | 376/252 |
| 5,523,058 | 6/1996 | Unemura et al. | 422/128 |
| 5,526,816 | 6/1996 | Arditi | 600/458 |
| 5,529,070 | 6/1996 | Augustine et al. | 600/443 |
| 5,531,224 | 7/1996 | Ellis et al. | 600/437 |
| 5,538,004 | 7/1996 | Bamber | 128/916 |
| 5,540,909 | 7/1996 | Schutt | 424/952 |
| 5,558,091 | 9/1996 | Acker et al. | 600/424 |
| 5,558,092 | 9/1996 | Unger et al. | 600/439 |
| 5,560,364 | 10/1996 | Porter | 600/458 |
| 5,566,674 | 10/1996 | Weng | 600/443 |
| 5,568,813 | 10/1996 | Dietrich et al. | 600/437 |
| 5,570,691 | 11/1996 | Wright et al. | 600/447 |
| 5,575,286 | 11/1996 | Weng et al. | 600/444 |
| 5,575,290 | 11/1996 | Teo et al. | 600/456 |
| 5,577,505 | 11/1996 | Brock-Fisher et al. | 600/458 |
| 5,579,768 | 12/1996 | Klesenski | 600/442 |
| 5,579,770 | 12/1996 | Finger | 600/442 |
| 5,580,575 | 12/1996 | Unger et al. | 424/450 |
| 5,582,173 | 12/1996 | Li | 600/443 |
| 5,588,435 | 12/1996 | Weng et al. | 600/443 |
| 5,590,659 | 1/1997 | Hamilton et al. | 600/447 |
| 5,601,085 | 2/1997 | Ostensen et al. | 600/458 |
| 5,601,086 | 2/1997 | Pretlow, III et al. | 600/458 |
| 5,606,975 | 3/1997 | Liang et al. | 600/462 |
| 5,608,690 | 3/1997 | Hossack et al. | 367/138 |
| 5,608,849 | 3/1997 | King, Jr. | 345/419 |
| 5,612,713 | 3/1997 | Bhuva et al. | 345/84 |
| 5,617,862 | 4/1997 | Cole et al. | 600/459 |
| 5,628,322 | 5/1997 | Mine | 600/453 |
| 5,632,277 | 5/1997 | Chapman et al. | 600/443 |
| 5,655,535 | 8/1997 | Friemel et al. | 600/443 |
| 5,678,554 | 10/1997 | Hossack et al. | 600/459 |
| 5,696,737 | 12/1997 | Hossack et al. | 367/138 |
| 5,699,805 | 12/1997 | Seward et al. | 600/459 |
| 5,704,361 | 1/1998 | Seward et al. | 600/459 |
| 5,713,363 | 2/1998 | Seward et al. | 600/437 |
| 5,724,976 | 3/1998 | Mine et al. | 600/459 |
| 5,724,978 | 3/1998 | Tenhoff | 128/916 |
| 5,735,281 | 4/1998 | Rafter et al. | 600/458 |
| 5,776,067 | 7/1998 | Kamada et al. | 600/443 |
| 5,797,849 | 8/1998 | Vesely et al. | 600/461 |
| 5,876,342 | 3/1999 | Chen et al. | 600/443 |
| 5,891,039 | 4/1999 | Bonnefous et al. | 600/454 |
| 5,899,861 | 5/1999 | Friemel et al. | 600/443 |
| 5,903,319 * | 5/1999 | Busko et al. | 382/300 |
| 5,920,660 * | 7/1999 | Goto | 382/300 |
| 5,933,547 * | 8/1999 | Dudon et al. | 382/300 |
| 6,059,727 | 5/2000 | Fowlkes et al. | 600/443 |

OTHER PUBLICATIONS

Powerpace Enhancement Package, product brochure (date unknown), 1 page.

U.S. application No. 08/874,792 filed Jun. 12, 1997. (This should be incorporated in the spec.).

Bom. N. et al., "Early and Recent Intraluminal Ultrasound Devices" (1989), pp. 79–88.

Rosenfield, K. et al., "Three Dimensional Reconstruction of Human Coronary and Peripheral Arteries From Images Recorded During Two–Dimensional Intravascular Ultrasound Examination" *Circulation* (1991) vol. 84, No. 5, pp. 1938–1956.

Gussenhoven, E. et al., "Displacement Sensing Device Enabling Accurate Documentation of Catheter Tip Position," *Intravascular Ultrasound* (1993), pp. 157–166.

O'Donnell, M. et al., "Synthetic Phased Array Imaging of Coronary Arteries with an Intraluminal Array," IEEE Ultrasonics Symposium (1995), pp. 1251–1254.

Shaulov, A. et al., "Biplane Phased Array for Ultrasonic Medical Imaging" (1988), pp. 635–638.

Chiang C. Mei et al., "Parametric resonance of a spherical bubble." J. Fluid Mech. vol. 229 (1991).

V.L. Newhouse et al., "Bubble size measurements using the nonlinear mixing of two frequencies." J. Acoust. Soc. am. 75 (5), May 1984.

Janet B. Jones–Oliveira et al., "Transient fluid—solid interaction of submerged spherical shells revisited: Proliferation of frequencies and acoustic radiation effects." Acoustical Society of America, 96(2) Pt. 1, Aug. 1994.

Chandra M. Sehgal, Ph.D. et al., "Sonographic Enhancement of Renal Cortex by Contrast Media." J. Ultrasound Med., 14 (1995).

"Abstract Session IV Contrast and Ischemia" and "Poster session A New Technologies." Journal of the American Society of Echocardiography, vol. 8, No. 3, May 1995.

Chandra M. Sehgal, Ph.D. et al., "Influence of Postprocessing Curves on Contrast—Echographic Imaging: Preliminary Studies." J. Ultrasound Med., 14 (1995).

Deborah J. Rubens, M.D. et al., "Sonoelasticity Imaging of Prostate Cancer: In Vitro Results." Radiology, vol. 995, No. 2 (1995).

Kotaro Sato et al., "Numerical analysis of a gas bubble near a rigid boundary in an oscillatory pressure field." J. Acoustical Society of America, 95 (5), May 1994.

L. W. Anson et al., "Ultrasonic scattering from spherical shells including viscous and thermal effects." J. Acoustical Society of America, 94 (4), Apr. 1993.

B. Schrope et al., "Simulated Capillary Blood Flow Measurement Using a Nonlinear Ultrasonic Contrast Agent," Ultrasonic Imaging 14 (1992).

Fred Lee, Jr., M.D. et al., "Sonoelasticity Imaging: Results in in Vitro Tissue Specimens." Radiology, vol. 181, No. 1 (1991).

Kevin J. Parker, Ph.D. et al., "Sonoelasticity of Organs: Shear Waves Ring a Bell." J. Ultrasound Med., 11 (1992).

William Armstrong, M.D. et al., "American Society of Echocardiography Position Paper on Contrast Echocardiography." Draft 1—Jun. 6, 1994.

K. J. Parker et al., "Tissue Response to Mechanical Vibrations for 'Sonoelasticity Imaging'." Ultrasound in Med. & Biol., vol. 16, No. 3 (1990).

Robert M. Lerner et al., "'Sonoelasticity' Images Derived from Ultrasound Signals in Mechanically Vibrated Tissues." Ultrasound in Med. & Biol., vol. 16, No. 3 (1990).

J. Ophir et al., "Elastography: A Quantitative Method for Imaging the Elasticity of Biological Tissues." Ultrasonics Imaging 13 (1991).

J. A. Hossack et al., "Improving transducer performance using multiple active layers." SPIE vol. 1733 (1992).

Volkmar Uhlendorf et al., "Nonlinear Acoustical Response of Coated Microbubbles in Diagnostic Ultrasound." 1994 Ultrasonics Symposium.

John A. Hossack et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

H. Edward Karrer et al., "A Phased Array Acoustic Imaging System for Medical Use." 1980 Ultrasonics Symposium.

"HP Ultrasound Technologies—Viability." About HP Ultrasound Imaging, WWW document (1997).

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

"Supplement to Journal of the American College of Cardiology" American College of Cardiology, 45th Annual Scientific Session, Mar. 24–27, 1996, pp. 21A, 63A, 239–240A.

Yang–Sub Lee et al., "Time–domain modeling of pulsed finite–amplitude sound beams." 1995 Acoustical Society of America, 97 (2), Feb. 1995.

Michalakis A. Averkiou et al., "Self–demodulation of amplitude–and frequency–modulated pulses in a thermoviscous fluid." J. Acoustical Society of America, 94 (5), Nov. 1993.

Nico de Jong, "Physical Properties and Technical Aspects of Ultrasound Contrast Agents." (one page).

"Small Spheres Lead to Big Ideas." Research News, Science vol. 267, Jan. 20, 1995.

Excerpt from Ultrasonics: Fundamentals and Applications (1992), pp. 380–393, 363–65.

Paul R. Detmer et al., "3D Ultrasonic Image Feature Localization Based on Magnetic Scanhead Tracking: In Vitro Calibration and Validation" (Ultrasound in Med. & Biol., vol. 20, No. 9, pp. 923–936, 1994).

Daniel F. Leotta et al., "Three–Dimensional Ultrasound Imaging Using Multiple Magnetic Tracking Systems and Miniature Magnetic Sensors." .

Bhaskar S. Ramamurthy et al., Potential Limitations of Angle–Independent Flow Detection Algorithms Using Radio–Frequency and Detected Echo Signals (Ultrasonic Imaging 13, 252–268, 1991, p. 252).

M. Belohlavek et al., "Multidimensional Ultrasonic Visualization in Cardiology" (Ultrasonics Symposium pp. 1137–1145, 1992).

Laurence N. Bohs, "A Novel Method for Angle Independent Ultrasonic Imaging of Blood Flow and Tissue Motion," (IEEE Transactions on Biomedical Engineering, vol. 38, No. 3, Mar. 1991).

Timothy C. Hodges et al., "Ultrasonic Three–Dimensional Reconstruction: In Vitro and In Vivo Volume and Area Measurement" (Ultrasound in Med. & Biol., vol. 20, No. 88, pp. 719–729, 1994).

Hugh A. McCann, et al. "Multidimensional Ultrasonic Imaging for Cardiology" (Proceedings of the IEEE, vol. 76, No. 9, Sep. 1988).

Elizabeth O. Ofili et al., "Three–Dimensional and Four–Dimensional Echocardiography" (Ultrasound in Med. & Biol., vol. 20, No. 8, pp. 669–675, 1994).

Dan Sapoznikov et al., "Left Ventricular Shape, Wall Thickness and Function Based On Three–Dimensional Reconstruction Echocardiography", (0276–6574/87; p. 495).

Shinichi Tamura et al., "Three–Dimensional Reconstruction of Echocardiograms Based on Orthogonal Sections" (Pattern Recognition; vol. 18, No. 2, pp. 115–124, 1985).

J. Souquet et al., "Transesophaegeal Phased Array for Imaging for the Heart" (IEEE Transactions on Biomedical Engineering, vol. BME–29, No. 10, Oct. 1982).

"L64720 Video Motion Estimation Processor" (MEP), LSI Logic.

"ISO/IEC Standard" (MPEG Video) Nov. 25, 1991.

Siemens Sonoline® Elegra Ultrasound Imaging Platform and Extended Filed View XFOV™ Imaging (Nov. 1995).

* cited by examiner

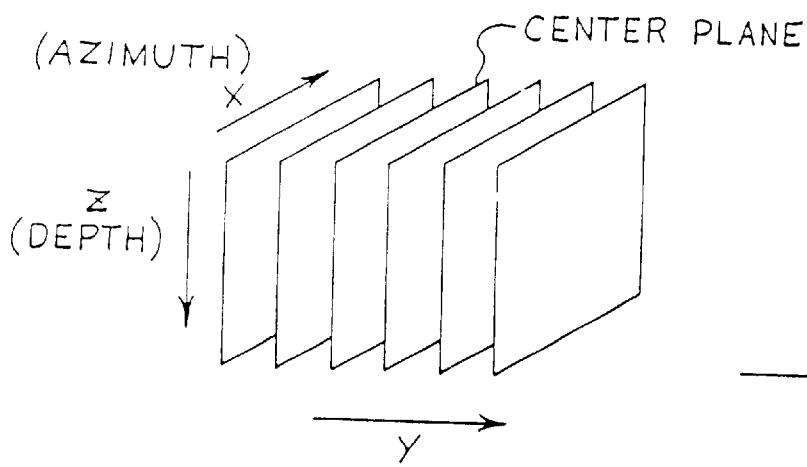
_Fig. 17_
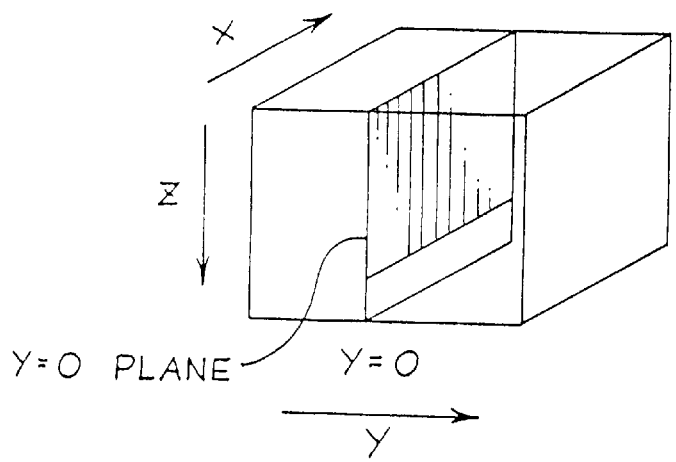
_Fig. 18_
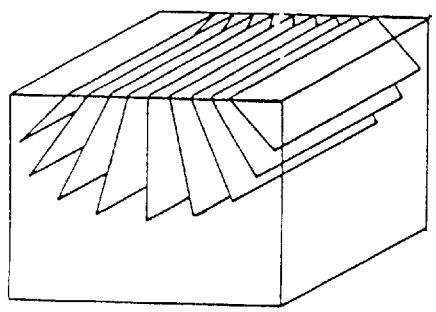
_Fig. 19_

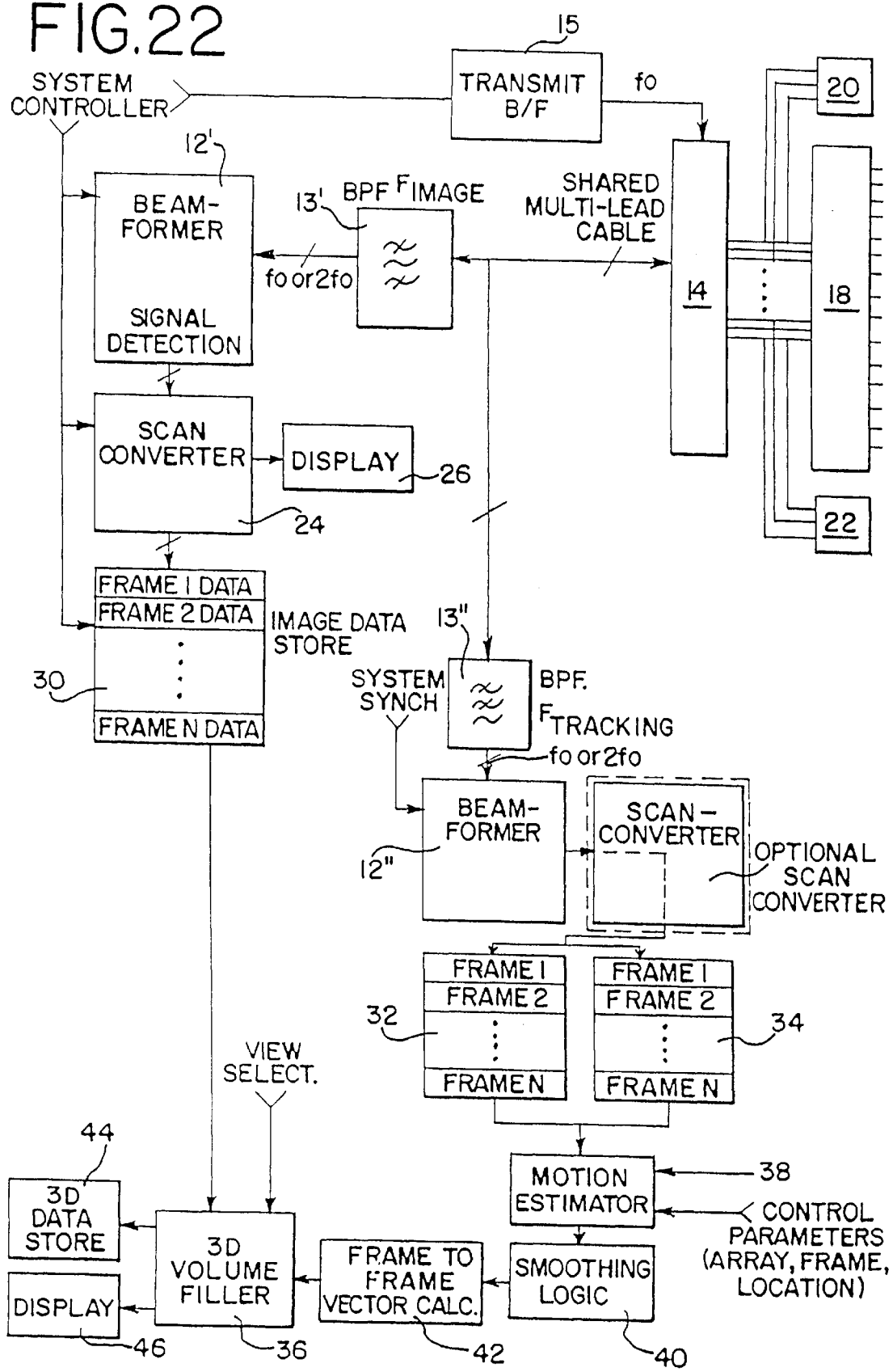

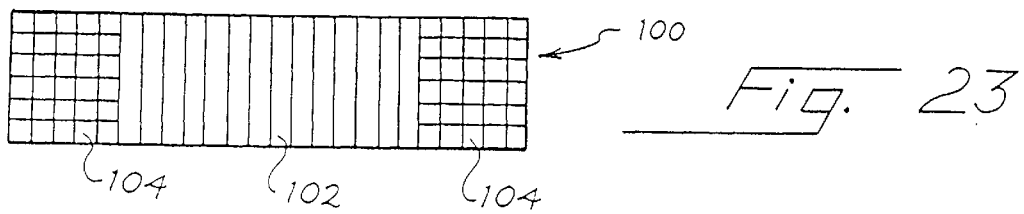
Fig. 23
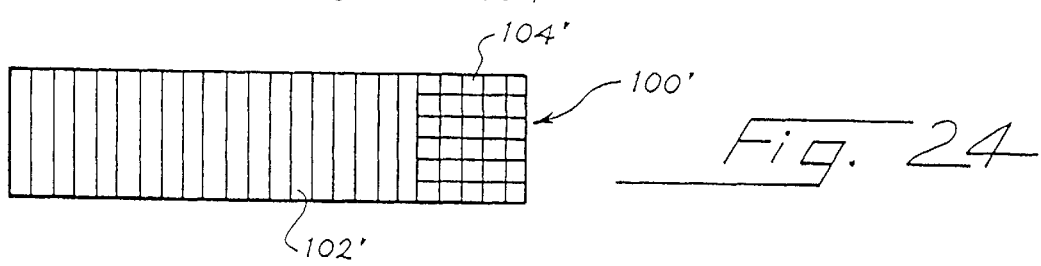
Fig. 24
Fig. 25
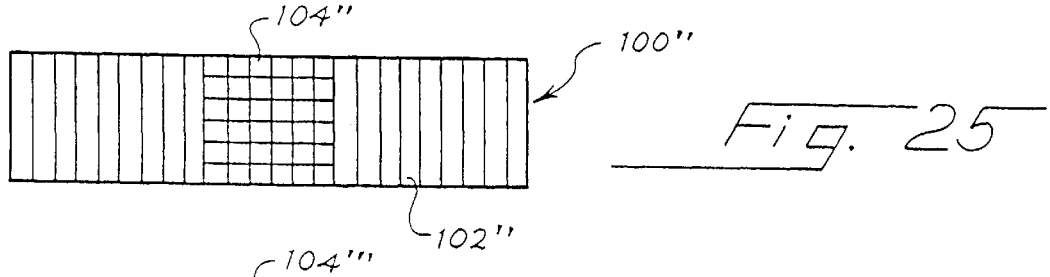
Fig. 26
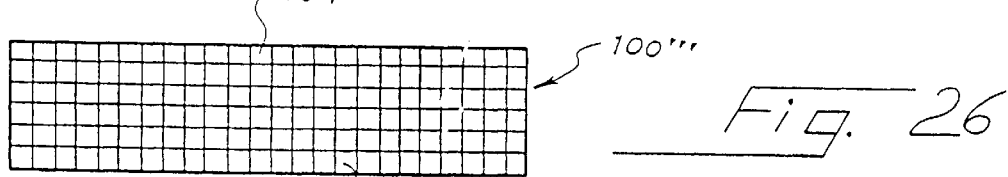
Fig. 27
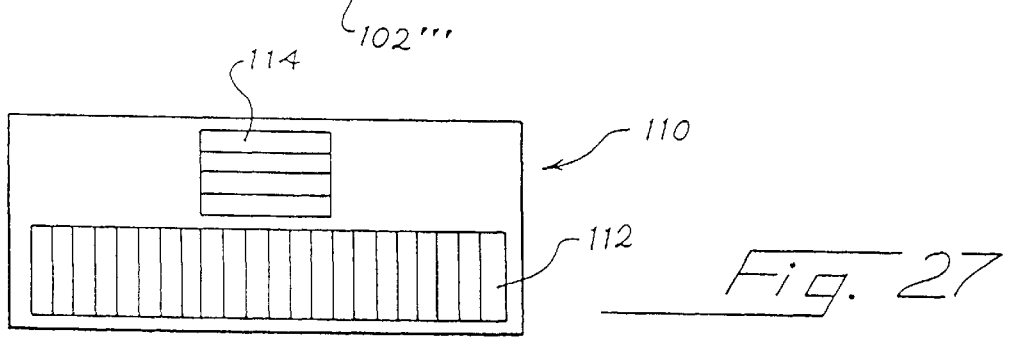
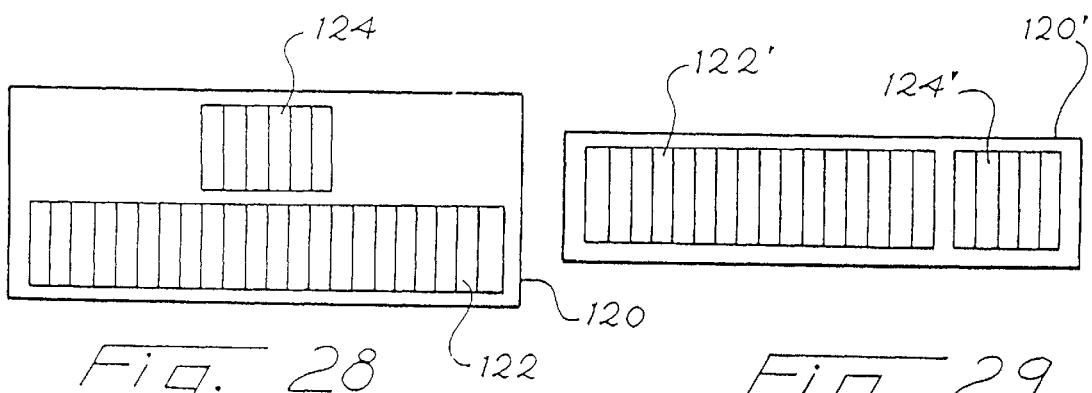
Fig. 28
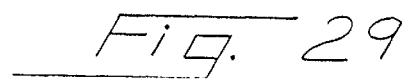
Fig. 29

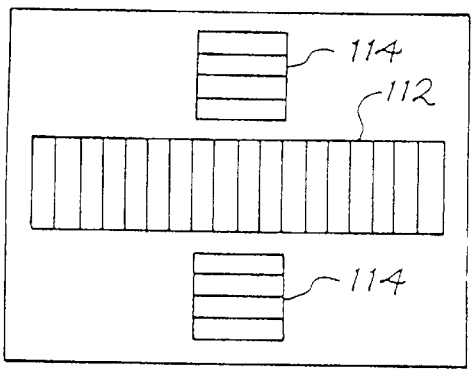
Fig. 27a
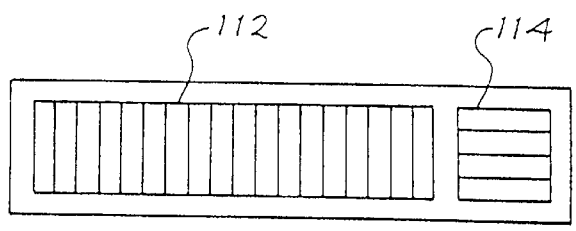
Fig. 27b
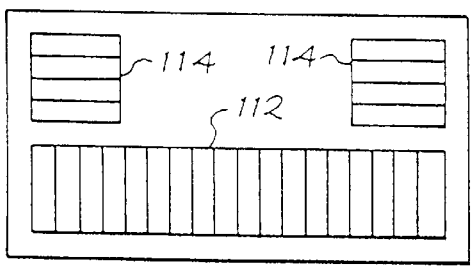
Fig. 27c
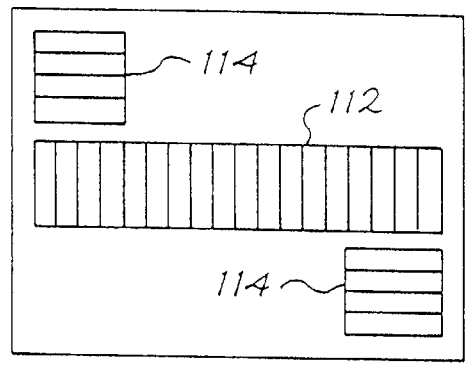
Fig. 27d
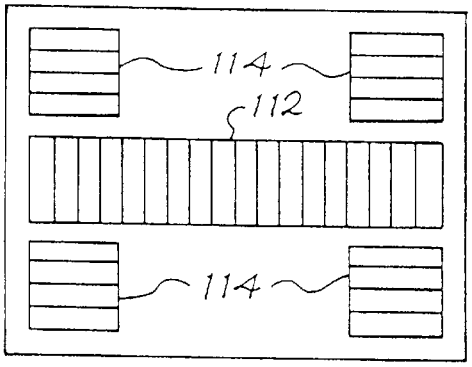
Fig. 27e
Fig. 38
| | OLD PORTION OF FRAME | | | | NEW PORTION OF FRAME | | | |
|---|---|---|---|---|---|---|---|---|
| PIXEL No. | 0 | 1 | 2 | 3 | 4 | 5 | 6 | 7 |
| FRAME 1 WEIGHTING FACTOR | 1 | 1 | .75 | .50 | .25 | 0 | 0 | 0 |
| FRAME 2 WEIGHTING FACTOR | 0 | 0 | .25 | .50 | .75 | 1 | 1 | 1 |

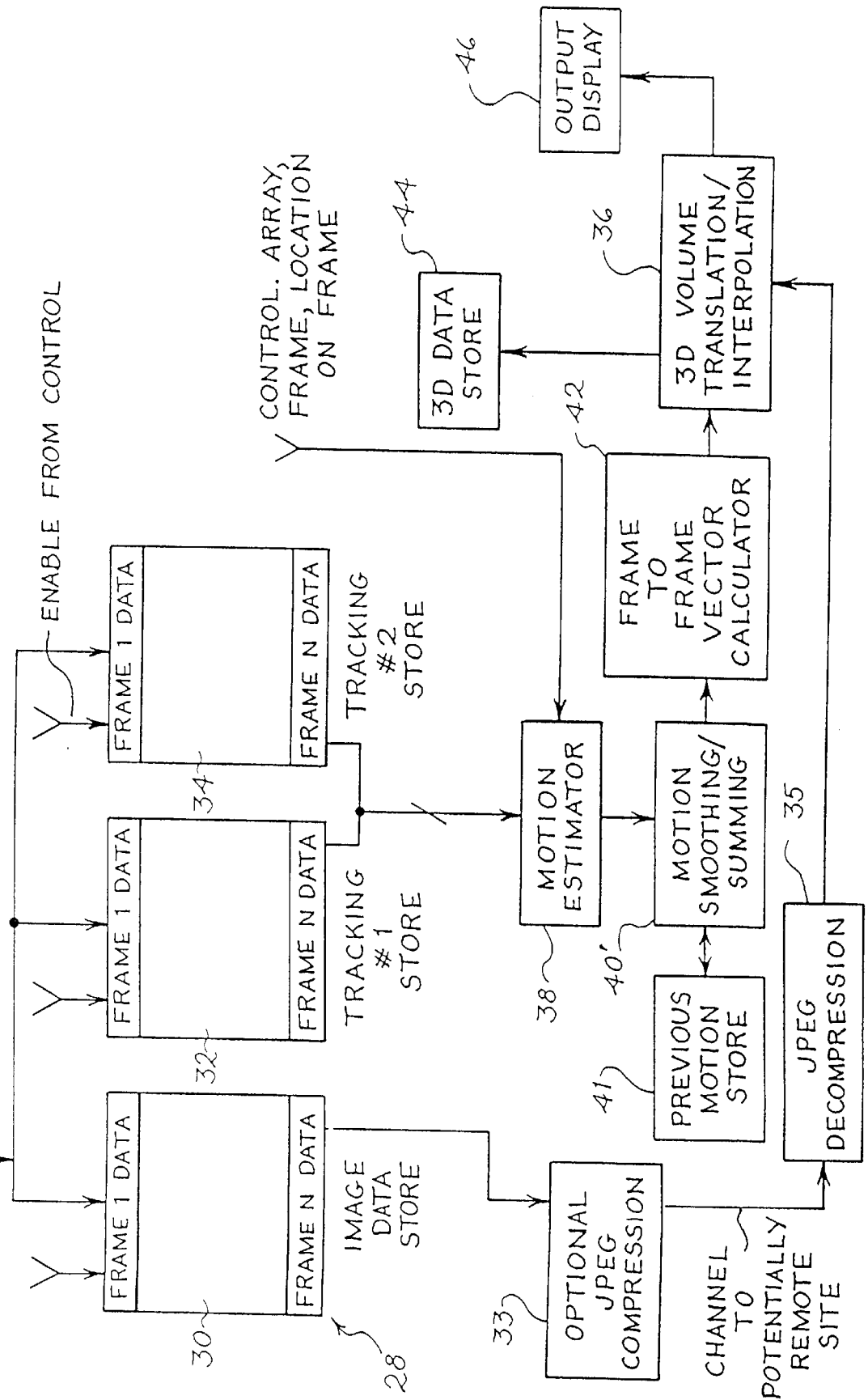

MULTIPLE ULTRASOUND IMAGE REGISTRATION SYSTEM, METHOD AND TRANSDUCER

CROSS-REFERENCE TO RELATED APPLICATION

This application is a division of application Ser. No. 08/915,885, filed Aug. 22, 1997, and which is now U.S. Pat. No. 6,014,473, issued Jan. 11, 2000.

This application is a continuation-in-part of U.S. patent application Ser. No. 08/621,561, filed Mar. 25, 1996 now abandoned, which is in turn a continuation-in-part of provisional U.S. patent application Ser. No. 60/012,578 filed Feb. 29, 1996, and assigned to the assignee of the present invention.

BACKGROUND OF THE INVENTION

This invention relates to an improved system, method and transducer for acquiring two-dimensional image information and relative positional information regarding the image information to allow subsequent three-dimensional or extended field of view reconstruction.

There is growing interest in three-dimensional ultrasonic images. One approach is to use a two-dimensional transducer array to obtain three-dimensional image information directly. A two-dimensional array can be used to scan electronically in any desired orientation, and thereby to acquire the desired information. This approach brings with it considerable problems related to fabrication difficulties, signal to noise difficulties and processing difficulties.

Another approach is to collect multiple two-dimensional image data frames using a one-dimensional transducer array along with relative positional information among the image data frames so that these frames may be subsequently assembled in a three-dimensional volume to form the desired three-dimensional reconstruction. One approach is to use a motorized array to collect the desired set of image data frames by precisely controlling the movement of the transducer array. One example is the transducer shown in U.S. patent application Ser. No. 08/267,318 (Hossack, et al., assigned to the assignee of the present invention). See also Pini U.S. Pat. No. 5,159,931). A related approach is to use a large rotating transducer as described in McCann et al., "Multidimensional Ultrasonic Imaging for Cardiology" (Proceedings of IEEE, 76, 9, pp. 1063–1072, Sep. 1988). Another approach is to use manual motion detection techniques based on analysis of ultrasonic images. See Sapoznikov et al., "Left Ventricular Shape, Wall Thickness and Function Based on Three-Dimensional Reconstruction Echocardiography" ("Computers in Cardiology," IEEE Computer Society Press, Cat CH 2476-0, pp. 495–498, 1987); and Taruma et al., "Three-Dimensional Reconstruction of Echocardiograms Based on Orthogonal Sections" (Pattern Recognition, 18, 2, pp. 115–124, 1985). Manual techniques are slow and cumbersome and, therefore have many drawbacks.

Schwartz U.S. Pat. No. 5,474,073 describes a qualitative three-dimensional method using a hand-held transducer array and an assumed scan motion. Qualitative methods have drawbacks, and the present invention is directed to a quantitative method.

Keller U.S. Pat. No. 5,353,354 discloses a transducer array equipped with accelerometers or magnetic sensors designed to measure the orientation of the transducer, and therefore relative motion between respective image planes. Once the image plane positional information is provided, standard methods are employed for assembling the image plane information into a three-dimensional volume and providing an appropriate display such as a cross section, a surface rendering, a segmentation, or the like. One drawback of the Keller approach is that it relies on assessing the position of the transducer array with respect to a fixed surface exterior to the patient, not with respect to the patient or other target. If the patient moves, the absolute position of all target regions is moved, and the accuracy of the three-dimensional reconstruction is degraded or eliminated entirely. Magnetic sensor systems have additional disadvantages, such as potential vulnerability to local magnetic interference from metal objects and electromagnetic fields generated by electronic devices such as cathode ray tubes. Accelerometer systems can be bulky and susceptible to cumulative error, since they rely on two stages of integration to convert acceleration information to displacement information.

The present invention is directed to a new system and transducer which to a large extent overcome the problems discussed above.

SUMMARY OF THE INVENTION

According to a first aspect of this invention, a method is provided for registering image information acquired from a target, comprising the following steps:

(a) acquiring a plurality of sets of image information with at least one ultrasonic transducer array, said at least one array moved between at least some of the sets of image information, said plurality of sets comprising a plurality of image data sets and a plurality of tracking sets;

(b) automatically determining a component of motion based on a comparison of at least a portion of the tracking sets acquired in step (a); and (c) automatically using the component of motion determined in step (b) to register selected ones of the image data sets acquired in step (a).

According to one aspect of this invention, the image data sets are acquired with different transducer arrays. According to another aspect of this invention, motion estimates are used to create an extended field of view, and in this case no separate array may be required for the tracking sets.

This invention is also directed to an improved transducer suitable for use in the method described below. The transducer of this invention includes a support element and first, second, and third transducer arrays coupled to move with the support element. The first transducer array includes first transducer elements arranged along an azimuthal axis and having first and second ends spaced along the azimuthal axis and a first central image plane. The second transducer array comprises second transducer elements positioned near the first end of the first transducer array and comprising a second central image plane. The third transducer array comprises third transducer elements positioned near the second end of the first transducer array and comprising a third central image plane. The first and second central image planes are non-parallel, as are the first and third central image planes.

This arrangement for an ultrasonic transducer allows both tracking information and image information to be collected concurrently. The tracking information is used to determine estimates of the movement of the transducer and/or the target between respective image data frames. This information can then be used in registering the respective image data frames appropriately in three-dimensions to form the desired three-dimensional representation.

Further aspects and advantages of the invention are discussed below in conjunction with the preferred embodiments.

BRIEF DESCRIPTION OF THE DRAWINGS

FIGS. 17, 18 and 19 are three schematic perspective views showing the manner in which multiple image data frames can be registered with respect to one another in three-dimensions to form a three-dimensional representation.

FIG. 22 is a schematic view of an alternative ultrasonic imaging system.

FIGS. 23 through 26 are plan views of transducers using crossed arrays suitable for use in selected embodiments of this invention.

FIGS. 27, 27a through 27h, and 27j are plan views of alternative transducers suitable for use in selected embodiments of this invention.

FIGS. 28 and 29 are plan views of other transducers suitable for use in selected embodiments of this invention.

FIG. 38 is a diagram showing the manner in which two frames can be weighted to form an extended field of view.

DETAILED DESCRIPTION OF THE PRESENTLY PREFERRED EMBODIMENTS

Figure 1:
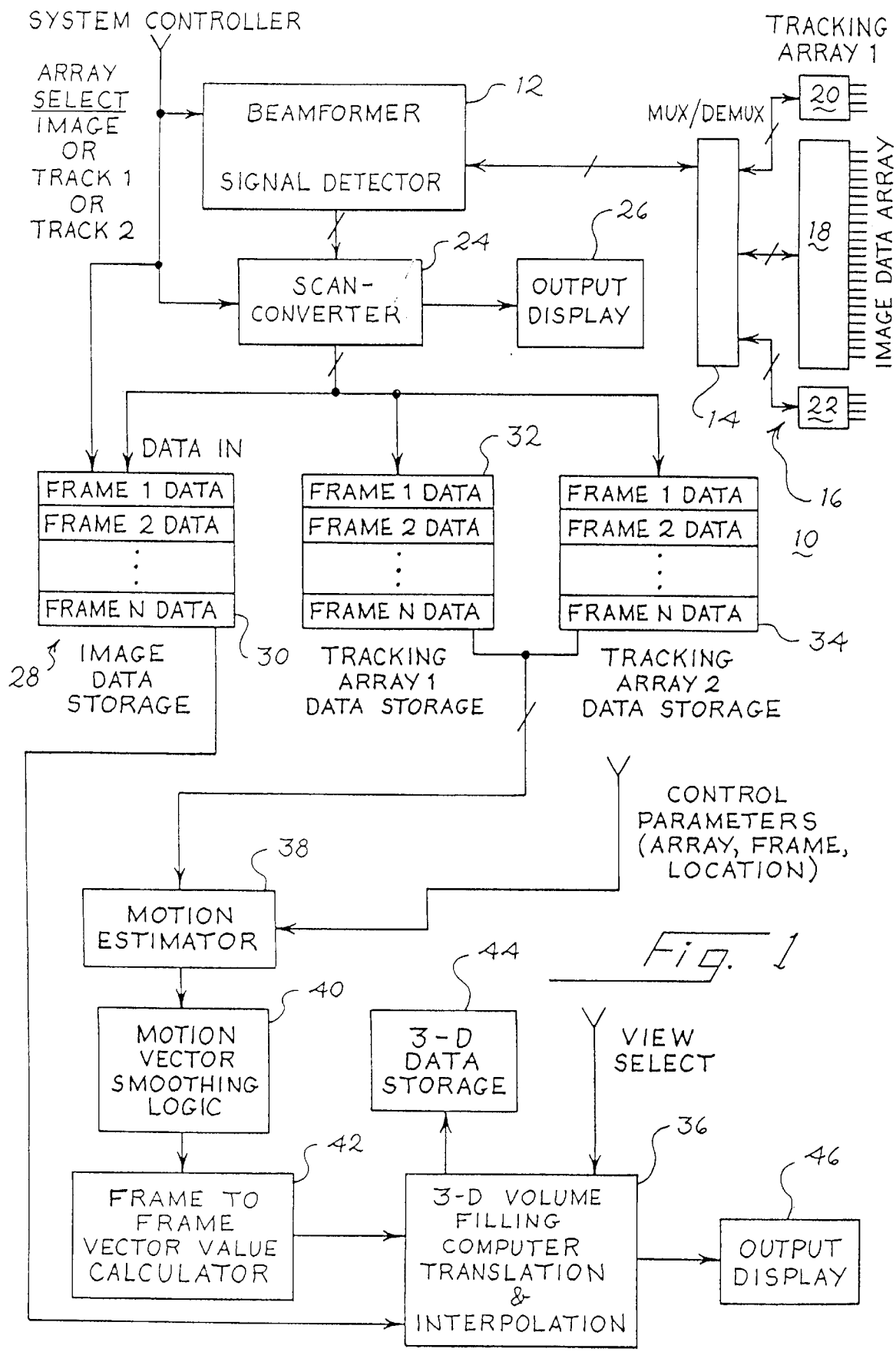
FIG. 1 is a block diagram of an ultrasonic imaging system that incorporates a presently preferred embodiment of this invention.

Turning now to the drawings, FIG. 1 is a block diagram of an ultrasonic imaging system 10 which incorporates a presently preferred embodiment of this invention. The following discussion will first present a system overview, and then a detailed description of selected components of the system.

System Overview

The system 10 includes a beamformer system/signal detector 12 which includes both transmit and receive beamformers and is connected via a multiplexer/demultiplexer 14 to an ultrasonic transducer 16. Any suitable devices, including conventional devices, can readily be adapted for use as the elements 12, 14.

The ultrasonic transducer 16 will be described in greater detail below in conjunction with FIGS. 2–4. Here, it is important to note that the transducer 16 preferably includes three separate transducer arrays 18, 20, 22. The array 18 is used for collecting image data that will be used to construct displayed representations of the target. The arrays 20, 22 are smaller arrays oriented in this embodiment at right angles to the image data array 18 to operate as tracking arrays. The tracking arrays 20, 22 are used in this embodiment to estimate the motion between respective image data frames from the image data array to allow the image data frames to be registered properly for reconstruction.

The beamformer system/signal detector 12 sends excitation signal pulses to the arrays 18, 20 and 22 and supplies summed returning echoes to a signal detector. The output of the signal detector is supplied to a scan converter 24. The beamformer system/signal detector 12 operates the arrays 18, 20, 22 in the conventional manner as phased arrays by properly timing the excitation signals applied to the arrays 18, 20, 22, and by properly timing and phasing the received signals prior to summing. The scan converter 24 controls an output display 26 to display preferably the three images generated by the three arrays 18, 20, 22 along with additional information as described below.

In addition, scan-converted image information from the scan converter 24 is stored in a data storage system 28. In this embodiment the data storage system 28 includes three separate storage arrays, each storing data for image frames from a respective one of the arrays 18, 20, 22. Thus, image information from the image data transducer array 18 is stored as frames of image data in the storage array 30, and image information from the tracking transducer arrays 20, 22 is stored as respective frames of image data in the storage arrays 32, 34, respectively. The frames of data in the storage arrays 30, 32, 34 are all time marked, so that they can be associated with one another appropriately. This time marking can take the form of real-time clock information or frame number information, for example.

The frames of image data in the storage array 30 are applied to a computer 36. It is these frames that are used to form the displayed representation of the target. The tracking image frames stored in storage arrays 32 and 34 are not registered to create a displayed reconstruction of the target, but are instead used to determine the relative positions of individual frames of image data from the image data storage array 30.

In order to estimate movement of the target between successive frames of the image data, the image information from the tracking array data storage arrays 32, 34 is supplied to a motion estimator 38. The motion estimator 38 compares sequences of images from the tracking transducer array 20 and the tracking transducer array 22 to estimate a component of motion of the transducer 16 between the respective frames. This estimate of the component of motion is smoothed in logic 40, and then applied to a calculator 42 that calculates a vector value defining the best estimate of the movement between selected frames of the image data stored in the image data storage array 30. This vector is then applied as another input to the computer 36.

Figure 20:
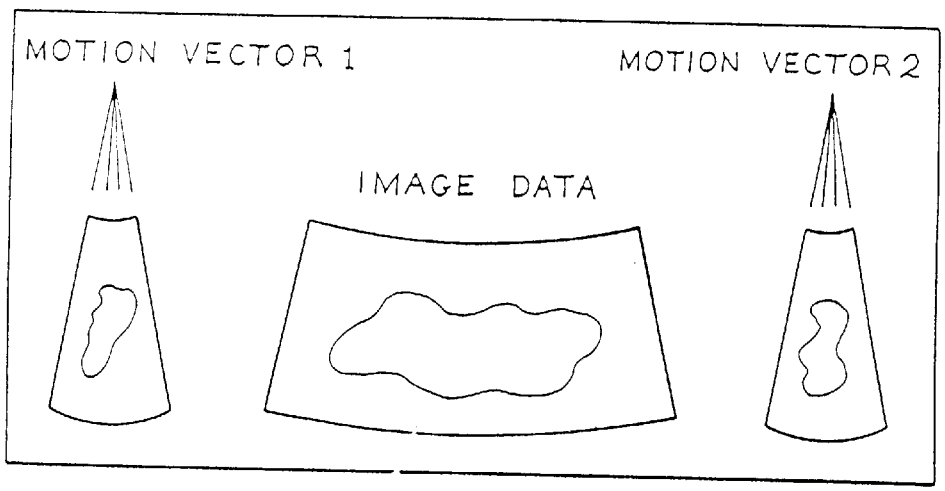
FIG. 20 is a view of a display generated by the system of FIG. 1.

In the system 10, the elements 28 through 42 can be designed to operate in real time, and the motion vectors can be displayed on the output display 26 as discussed in conjunction with FIG. 20. Once a full set of data has been acquired, the image data frames and the frame-to-frame translation vectors can then be transmitted to the specialized computer 36 which can either be combined with or external to the ultrasonic imaging system.

The computer 36 registers selected frames of image data from the image data storage array 30 with respect to one another by appropriate use of the vectors supplied by the calculator 42. Also any necessary interpolation is done, and the respective frames of image data are stored in proper registration with respect to one another in a three-dimensional data storage device 44. The computer 36, when operating in a display mode, can select appropriate information from the three-dimensional data storage device 44 to provide a desired image on the display 46. For example, cross sections can be taken in various planes, including a wide variety of planes that do not correspond to the planes of the image data. Also, surface renderings and segmentation displays can be created if desired.

In one mode of operation, the transducer 16 is rotated through a sweep under the direct manual control of an operator, smoothly from side-to-side about a single axis of rotation lying along the azimuthal axis on the face of the image data array 18. The method described below can account for imperfections in the sweep. During three-dimensional reconstruction, the quality of the reconstruction degrades gracefully as a result of positional error. Distortion rather than blurriness is the result of imperfect motion detection.

The Ultrasonic Transducer 16

Figure 2:
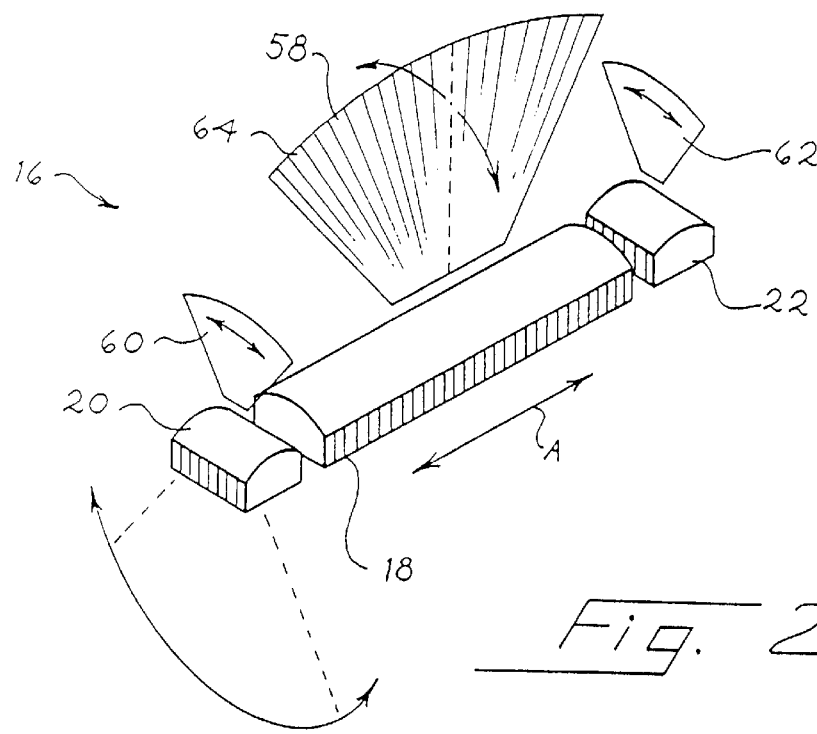
FIG. 2 is a schematic perspective view of the transducer of FIG. 1.
Figure 3:
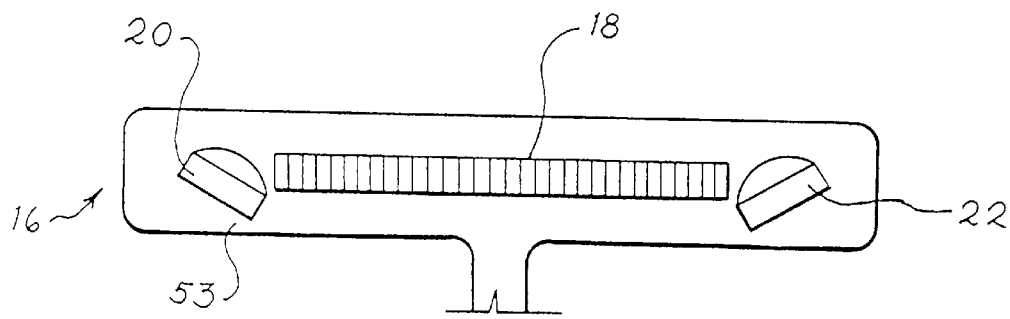
FIG. 3 is a schematic side view of the transducer of FIG. 2.
Figure 4:
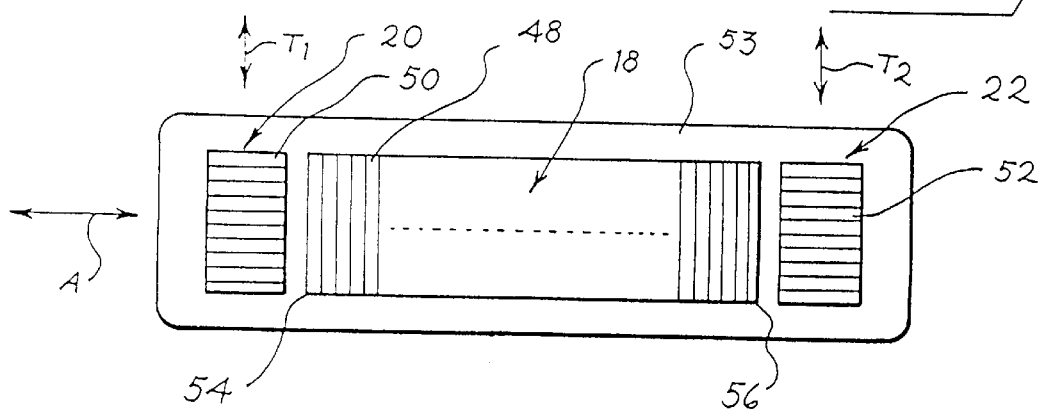
FIG. 4 is a schematic plan view of the transducer of FIG. 2.

FIGS. 2–4 provide three views of the ultrasonic transducer 16. As shown in FIG. 4, the three arrays 18, 20, 22 each comprise a respective set of transducer elements 48, 50, 52, all mounted on a common support element 53. The transducer elements 48 are arranged along an azimuthal axis A, and the image data transducer array 18 defines first and second ends 54, 56. The tracking arrays 20, 22 are each positioned near a respective one of the ends 54, 56, centered on the azimuthal axis A. The transducer elements 50, 52 are arranged along respective tracking axes T1, T2, and the tracking axes T1, T2 are in this preferred embodiment substantially perpendicular to the azimuthal axis A. The tracking arrays 20, 22 are each shorter than the image data array 18, and each has fewer transducer elements 50, 52. Each of the transducer elements 48 can be spaced at 1/N times the pitch of the transducer elements 50, 52. As shown in FIG. 3, the tracking arrays 20, 22 can be oriented to point inwardly, toward the image data array 18. Alternately, the tracking arrays 20, 22 can be coplanar with the array 18, to provide a preferred profile for the transducer 16.

The image data array 18 can be of conventional form, such as a flat linear array with a cylindrical elevation focusing lens. Alternately, the array can be generally flat, but the transducer elements can be curved in elevation to focus. In this case a non-refractive filler such as a polyurethane can be used since a focusing lens is no longer required. Whether or not a lens is used, the image data array may be curved in azimuth to yield a larger field of view. The tracking arrays 20, 22 will typically include a lens to achieve the desired focus in elevation. Since the curvatures of the various lenses or arrays will be in differing planes, a non-refractive filler section may be formed on the transducer 16 to yield the preferred smooth shape. Alternately, the tracking arrays 20, 22 may also be curved with non-refractive windows formed on top of the desired shape. Both the image data array 18 and the tracking arrays 20, 22 may be phased sector, Vector®, linear or curvilinear. All imaging modes including B mode, color Doppler, color Doppler energy and the like are supported. A conventional TEE transducer such as the biplane V510B transducer of Acuson can be used in a two-transducer embodiment.

The transducer geometry shown in FIGS. 3 and 4 can be used to obtain image planes as shown in FIG. 2. The image plane 58 of the image data array 18 in this embodiment passes through the azimuthal axis A. Image data collected with the image data array 18 is positioned along scan lines 64 in the image plane 58. The image planes 60, 62 of the transducer arrays 20, 22, respectively, are oriented transversely to the image plane 58. The image planes 58, 60, 62 are the central image planes of the respective arrays, that is the only image plane for a 1 D array and the central plane (i.e. the plane not steered in elevation) for a 1.5 D array.

For the sake of simplicity, the tracking arrays 20, 22 may have identical transducer element pitches to that used by the image data array 18. This approach allows the same beamformer delays to be used for all three arrays 18, 20, 22. However, in many applications the tracking arrays 20, 22 are adapted to form relatively fewer acoustic lines. This is particularly the case if motion detection is concentrated in the vicinity of the center line of the image planes 60, 62. If only a narrow field of view is required for the tracking arrays 20, 22 then the tracking array pitch may be coarser, for example twice the pitch of the image data array 18.

Figure 5:
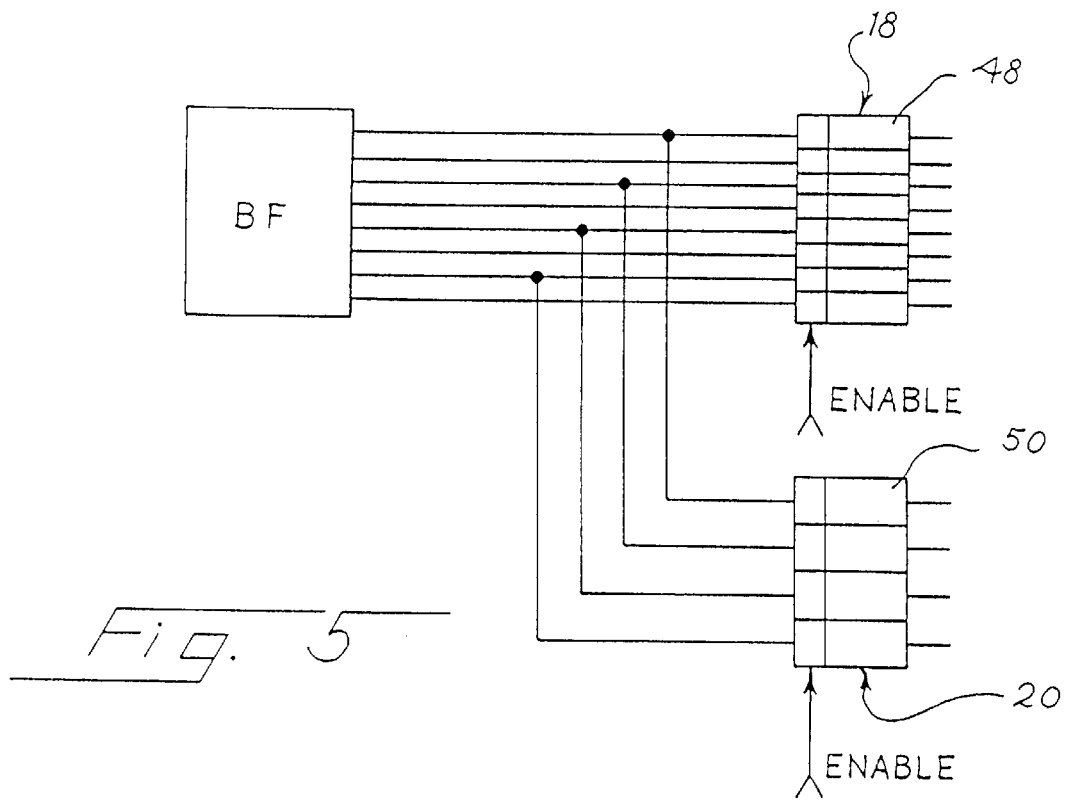
FIG. 5 is a schematic view of a portion of the system of FIG. 1.

By making the tracking array pitch an integer multiple of the image data array pitch, the same beamforming delays can be used, but with the appropriate channels disconnected, as shown in FIG. 5. In FIG. 5 the element-to-element pitch of the tracking array 20 is twice that of the image data array 18, and consecutive transducer elements 50 of the tracking array 20 are connected to only the even or odd signal lines for the transducer elements 48 of the image data array 18. In the limit, each tracking array 20, 22 may be composed of as few as two transducer elements, although this will limit the maximum resolution that is achievable.

Common signal conductors can be used between the beamformer/signal detector 12 and the housing for the transducer 16. In the housing, individual signals are routed between the signal conductors and the transducer elements 48, 50, 52 by high voltage analog switches or multiplexers, such as those available from Supertex Inc., Sunnyvale, Calif. and having the family designation HV2xx.

Figure 6:
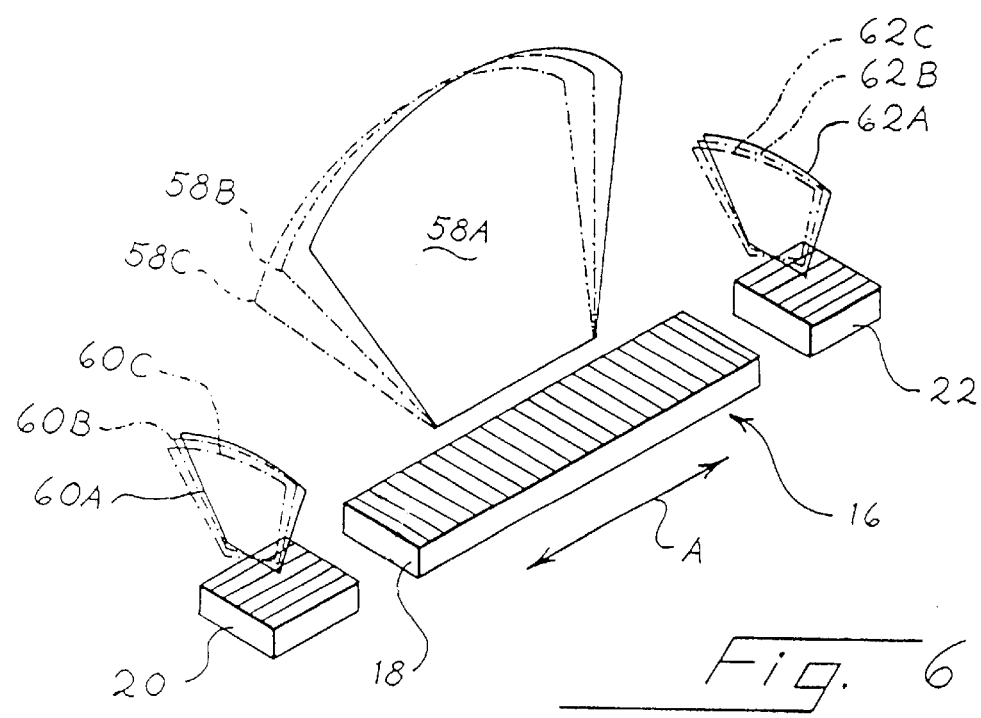
FIG. 6 is a schematic perspective view showing the movement of image regions as the transducer of FIG. 2 is rotated about the azimuthal axis.
Figure 7:
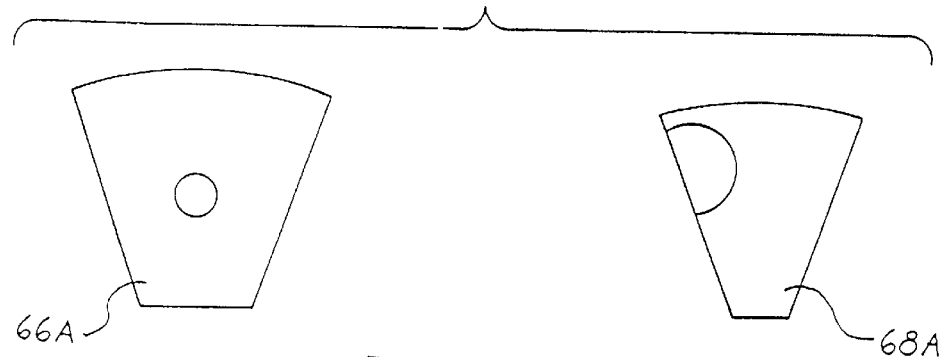
FIGS. 7, 8, 9 and 10 are schematic views showing images acquired with the transducer of FIG. 6 at four rotational positions of the transducer.
Figure 8:
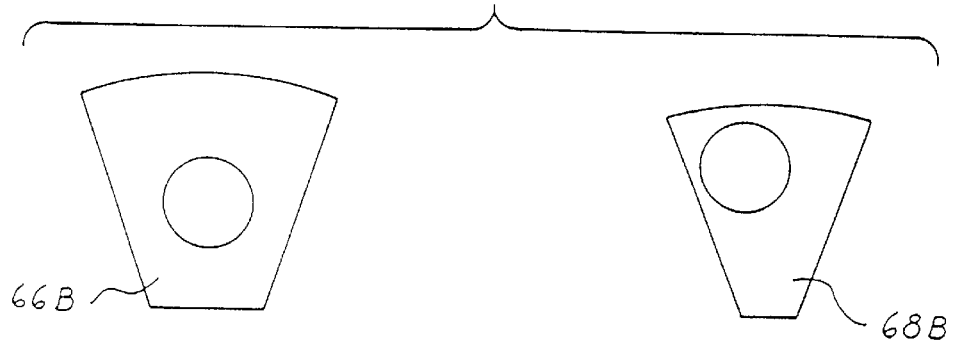
Figure 9:
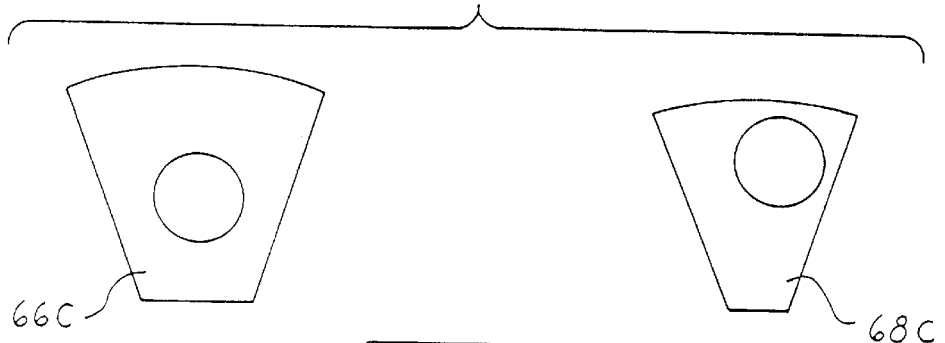
Figure 10:
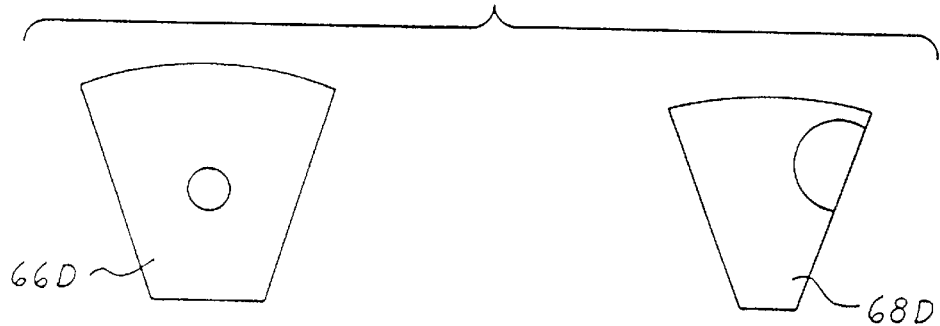

FIGS. 6–11 are schematic views that illustrate the manner in which images generated by the tracking arrays 20, 22 can be used to estimate the movement between images generated with the image data array 18. FIG. 6 shows a perspective view for three separate positions of the transducer 16. These three separate positions of the transducer 16 are obtained by rotating the transducer 16 about the azimuthal axis. As the image data array 18 rotates about the azimuthal axis A, the image planes 58A, 58B, 58C rotate in a fan-like manner. Thus, each of the image planes 58A, 58B, 58C of FIG. 6 is disposed in a separate, respective plane of three-dimensional space.

In contrast, the image planes 60A, 60B, 60C; 62A, 62B, 62C for each tracking array 20, 22 remain coplanar as the transducer 16 is rotated about the azimuthal axis A. The actually imaged regions within the image planes 60A, 60B, 60C; 62A, 62B, 62C rotate about the azimuthal axis A as the transducer 16 rotates. In many applications, the imaged regions within the image planes 58A, 58B, 58C will not overlap or intersect the imaged regions within the image planes 60A, 60B, 60C or the imaged regions within the image planes 62A, 62B, 62C. This arrangement can reduce cross talk and other interference problems, as discussed below.

FIGS. 7–10 show four sets of images. Each set includes an image 66A, B, C, D from the image data array 18 and a corresponding image 68A, B, C, D from one of the tracking arrays 20, 22. In this case the target is a sphere, and the images 66, 68 intersect such that the sphere appears in both Images 66, 68. As shown in images 66A, B, C, and D, various cross sections of the sphere are displayed as the transducer 16 rotates about the azimuthal axis. The cross sections shown in images 66A and 66D show smaller diameter disks taken near an edge of the sphere, and the images 66B and 66C show larger diameter disks taken near the center of the sphere. Thus, the disks shown on the images 66A, B, C and D differ in diameter, in accordance with the moving plane of the image (see FIG. 6). In contrast, the images 68A, B, C, and D all show disks of the same size. Because the plane of the images 66A, B, C, and D remains the same, as discussed above in conjunction with FIG. 6, the disk that is displayed in these images remains constant in size but moves across the image plane. The location of the disk as it moves from one image to the next provides a measure of a component of motion of the transducer 16 in the image plane of the images 68A, B, C, D.

If the image plane of the transducer arrays 20, 22 are not perpendicular to the surface of the image data array 18 (for example because the tracking arrays 20, 22 are pointed inwardly as shown in FIG. 3), it may be preferred to use a cosine Θ correction factor to take account of the difference between image range and physical depth perpendicular to the image data array 18.

Figure 11:
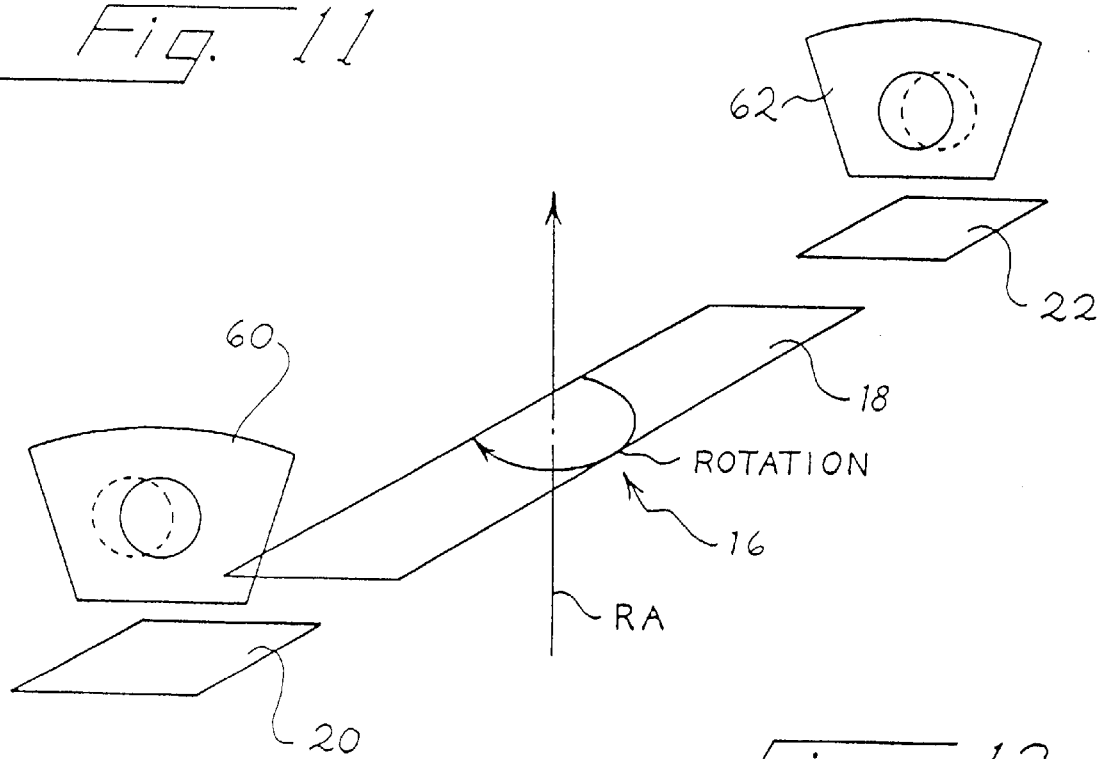
FIG. 11 is a schematic perspective view showing the operation of the transducer of FIG. 2.

An important advantage of the transducer 16 is that it includes two tracking arrays 20, 22, each positioned near an adjacent end 54, 56 of the image data array 18. This arrangement allows compound rotations to be assessed. In FIG. 11 the transducer 16 is rotated about a rotational axis RA oriented as shown. In FIG. 11 the solid-line circles denote the image of the target at a first point in time, and the dotted-line circles denote the image of the target at a subsequent point in time, after rotation about the rotational axis RA. Note that the images move in opposite directions in the image planes 60, 62 in this situation. By comparing the component of motion determined separately from the two tracking arrays 20, 22 the actual rotation of the target with respect to the transducer 16 can be determined.

Figure 21:
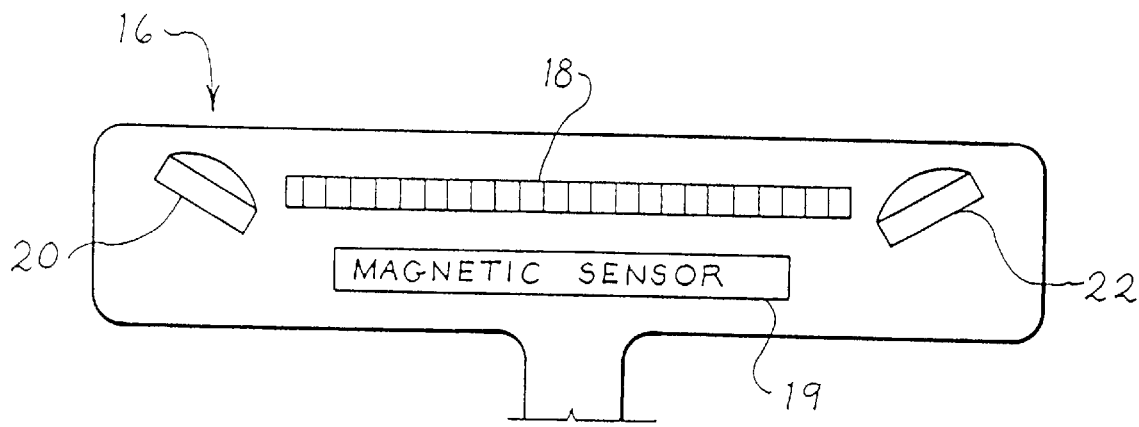
FIG. 21 is a schematic view of a modified version of the transducer of FIG. 1.

If desired, the transducer 18 can include an absolute sensor for position, orientation, or both, such as a magnetic sensor 19 as shown in FIG. 21 or an accelerometer. The sensor 19 may be used to supplement or back up the motion detection approach described in detail below, and may be of the types described in Keller U.S. Pat. No. 5,353,354.

The Beamformer System/Signal Detector 12

As the transducer 16 is rotated substantially about the azimuthal axis A, the image data array 18 and the tracking arrays 20, 22 are sequentially operated. When the arrays 18, 20, 22 are individually addressable, the transmit beamformer in element 12 sends appropriately timed and phased excitation signals to the respective transducer elements 48, 50, 52. In one embodiment a frame of data from the image data array 18 is collected, and then frames of data from the tracking arrays 20, 22 are collected. Alternately, the transmit beamformer may alternate between the image data array 18 and the tracking arrays 20, 22 between individual scan lines or between groups of scan lines. If the image planes of the arrays 18, 20, 22 are non-intersecting, and particularly if the image data array 18 is excited at a different frequency than the tracking arrays 20, 22, then the risk of cross-array interference is small. For this reason the pulse repetition rate (which is normally limited by the time required for ultrasonic signals to attenuate in the body between successive scan lines) may be increased.

In some applications the arrays 18, 20, 22 may be connected in common to the transmit beamformer. Typically, the imaging requirements for the image data array 18 will differ substantially from those for the tracking arrays 20, 22. Image data quality should be maintained at a high level, but tracking data need only be of sufficient quality to permit reliable tracking. Costs may be reduced by sharing some cable conductors between the array 18 and the arrays 20, 22. Typically, elements near the ends of the image data array 18 are most suitable for sharing, since they are less important than center elements.

In order to reduce interference between the arrays 18, 20, 22 cable routing from the elements 48 of the image data array 18 to the elements 50, 52 of the tracking arrays 20, 22 is preferably jumbled in a known pseudo-random manner. The element 12 uses the jumbling scheme to sort the beamformer delays such that one set of arrays (either the image data array 18 or the tracking arrays 20, 22) is operated coherently at any given scan line. The other set is operated incoherently because of the cable jumbling. The optimum jumbling scheme may be determined by routine experimentation.

Cross talk may be further reduced with frequency coding and voltage level techniques. The tracking arrays 20, 22 may operate with a reduced image depth, such as a few centimeters, and therefore a high frequency such as 10 MHz. The image data array 18 may operate at a longer range, lower frequency such as 5 MHz, thereby reducing cross talk. The transducer elements 48, 50, 52 may be formed with thicknesses that select the appropriate frequencies. Also, bandpass filters may be used in the element 12 to select the desired frequency bands for detection.

Voltage levels may vary between the two sets of arrays 18, 20, 22. For example a higher voltage may be used when the tracking arrays 20, 22 are selected, particularly if the tracking arrays 20, 22 require a higher voltage to operate effectively. In this case the tracking arrays 20, 22 emit a relatively small signal when the image data array 18 is selected and the voltage level is reduced.

FIG. 22 shows an alternative system 10' which uses many of the same components as the system 10. The system 10' differs in that the arrays 18, 20, 22 are operated simultaneously at different frequencies by beamformer/signal detectors 12', 12". In each case a respective bandpass filter 13', 13" is provided to isolate the bandpass of interest. As described above, the tracking arrays 20, 22 may operate at 10 MHz and the image data array 18 may operate at 5 MHz. The jumbled cable routing discussed above may be used to reduce interference. The bandpass filters 13', 13" can operate on beamformed signals, but the arrangement of FIG. 22 is preferred in practice.

When the transducer 16 is swept by rotating it about the azimuthal axis A, the preferred format for the image data array 18 is the sector format. Acoustic line data acquired by in the sector format can be conveniently used in the correlation process without scan conversion, since, for example, a pure rotation in rectangular coordinates can be represented as a change in an angular coordinate in a suitably chosen cylindrical coordinate system, given knowledge of the line to line angular increment, the angles of the lines with respect to the normal line (see FIG. 15), and the sample to sample range increment.

The Motion Estimator 38

Motion detection may be performed manually, for example by placing a line on the display data at a particular recognizable feature in the image planes 60, 62 and then repeating this activity on subsequent frames. The system can keep track of the line position for successive frames to generate a vector indicative of frame-to-frame motion.

A better method is to use computer analysis of frame-to-frame motion using a cross correlation or similar method on the image data acquired with the tracking arrays 20, 22. Such techniques (which will be referred to herein generally as correlation techniques) have been used in the past for tracking blood flow. These methods do not require that a recognizable feature be present in the display area, and they can function adequately using only ultrasound speckle data. Speckle is a naturally occurring phenomenon in ultrasound images and is a result of the coherent nature of the reflected waves from small scattering objects in the tissue.

Any suitable correlation technique can be used, including cross correlation and the sum of absolute differences method as discussed in Bohs and Trahey "A Novel Method For Angle Independent Ultrasonic Imaging Of Blood Flow And Tissue Motion" (IEEE Trans. on Biomed. Eng., 38, 3, pp. 280–286, March, 1991). Cross correlation is the well-known mathematical operation which uses sequentially obtained sums of multiplication operations for various translations of data in a search for the translation for which the two sets of data are best matched. The sum of absolute differences method is a computationally simpler correlation technique, but it achieves a similar net effect. The sets of data are translated by varying amounts. For each translation respective data values in each of the sets are subtracted and the sum of the absolute differences is calculated. If a particular translation gives a sum of absolute differences that is close to zero, then it is probable that the sets of data have been aligned by the associated translation. This translation required to achieve an alignment is an indication of the motion between the two respective frames at the sides of the image closest to the respective tracking array. As explained below, the motion at other parts of the image can be evaluated using the detected motion at both tracking arrays and linear interpolation techniques along the azimuth of the image data array 18.

The size of the data block used in either type of correlation is a matter for optimization. Bigger blocks will have a reduced likelihood of a false match but will require longer calculation times. The maximum frame-to-frame displacement that can be detected is limited by the block size. Typically, searches are made to plus or minus one-half of a block size. By way of example, a 16×16 pixel block may be used to detect a maximum translation of plus or minus 8 pixels.

The motion estimator 38 can use any effective technique to determine motion based on the frames of data stored in the arrays 30, 32, 34. Motion estimation may be based on the entire frame or on portions of the frame. When portions are used, they may be selected to correspond to a well-defined feature in the image. Motion estimation may be used on a spaced subset of available data to save time if that is more efficient. For example, if samples are available on a 0.5 mm spacing, but optimized motion detection can be performed based on a 1 mm spacing, time can be saved by deleting alternate samples and performing motion detection based on only a subset of the available data.

The tracking image data used for the motion estimation may take any one of a number of forms, including at least the following:

1. Adjacent pixels in the output display (which is interpolated from the actual acoustic line data);
2. Selected pixels from a larger grid, such as every Nth pixel;
3. Averages of groups of pixels, such as the average of a group of four adjacent pixels;
4. Samples from pre-scan conversion beamformer acoustic line data.

The beamformer outputs lines of acoustic data may be in polar or cartesian format. Since the relation between these lines of data and the physical lines of propagation are known, samples derived from these acoustic lines may be used in the motion detection.

Figure 15:
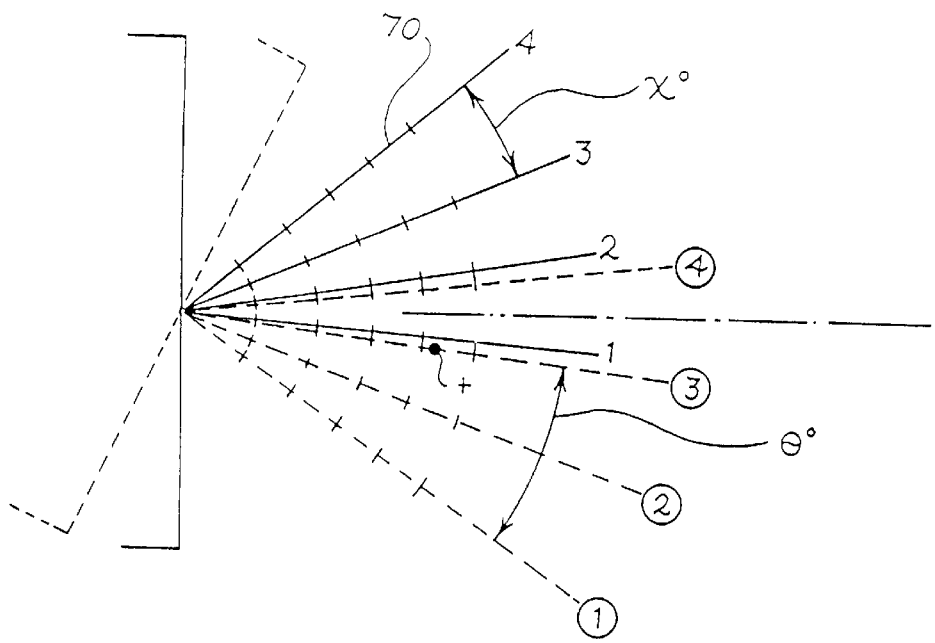
FIG. 15 is a schematic view showing the movement of the target among acoustic lines as the transducer of FIG. 2 is rotated about the azimuthal axis.
Figure 16:
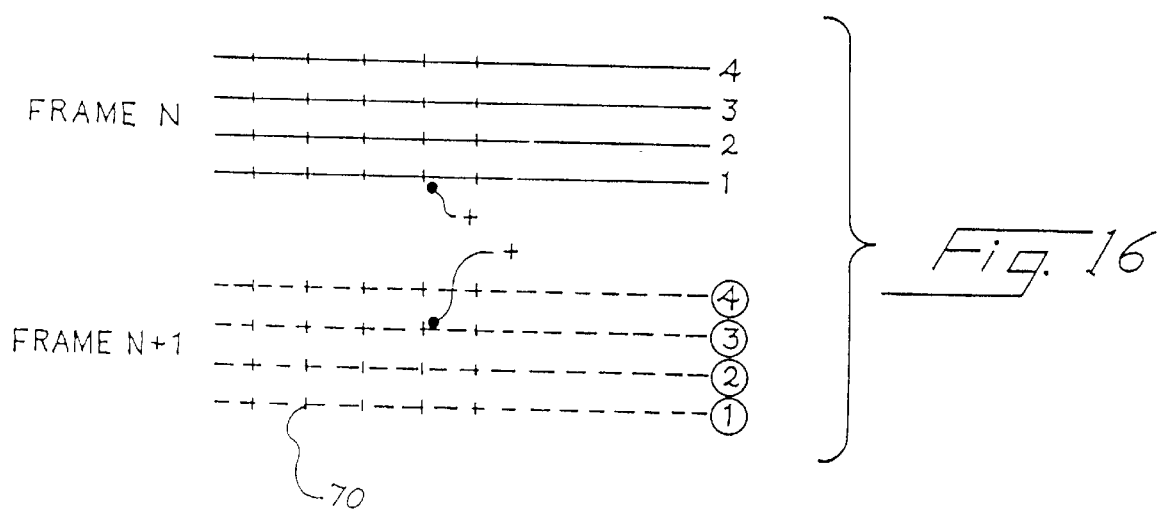
FIG. 16 is another view of the raw acoustic line data of FIG. 15.

FIG. 15 is a schematic view showing the position of a target at frames N and N+1 with respect to acoustic scan line data. In FIG. 15 reference symbol 70 is used for individual points at which the measurements were taken. These points are arranged at discrete intervals along the scan lines. FIG. 16 shows the raw acoustic line data (prior to scan conversion), in which each row represents a respective scan line, and the points of measurement at respective ranges are as illustrated. In FIGS. 15 and 16 the + symbol is used for the position of the target for both frames N and N+1. The motion estimator 38, when operating on frames N and N+1, detects that the target has moved from scan line 1 to scan line 3 and the range has remained constant at four sample intervals from the origin. Since the scan lines are spaced at an angular separation of X degrees and the distance between adjacent points 70 at the center of the motion block is equal to P millimeters, basic geometrical relationships can be used to prove that the lateral offset equals +8P sin×sin $\Theta$ and the depth offset equals −8P sin×cos $\Theta$, where $\Theta$ is the angle in degrees between the center of the motion detection block and the normal line emanating from the scan line origin, and where the tracking array is operating in sector format. These calculations are approximate, but they demonstrate the manner in which raw acoustic line data can be used in the motion estimator 38.

When acoustic line data is used in the motion estimator, it can correspond to digitized RF, digitized IF, digitized baseband, or rectified low-pass-filtered, envelope-detected signals. As an example of envelope-detected signals, B-mode data can be used. The acoustic line data signals may be real digital samples or complex (I, Q) data samples.

In the presently preferred embodiment the approach used in the motion estimator 38 relies on the sum of absolute differences in a pixel block equal to 16×16 pixels. For reasons of efficiency it is convenient to use a specialized integrated circuit. The LSI Logic 64720 integrated circuit is designed to perform 16×16 motion detection at rates of up to 396 blocks in 1/30th of a second. These circuits may be combined to yield higher throughput or larger block sizes. If the block size is reduced to 8×8 pixels, still higher rates are possible (4500 blocks in 1/30th of a second). This integrated circuit has the cost benefits of volume manufacture. Similar alternative integrated circuits may also be used. Alternatively, the entire operation can be performed using a suitably programmed general purpose processor such as the Texas Instruments TMS 320C80.

Preferably, the arrays 18, 20 are aligned with the array 16 such that the image plane 58 is aligned with the vertical axis of the image planes 60, 62. For this reason, motion with respect to the centerline of the image planes 60, 62 can be used to determine the relative motion of the image plane 58. Data blocks are defined lying along the center line.

Figure 13:
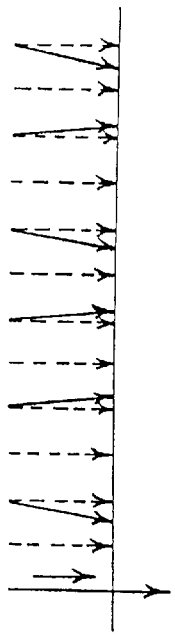
FIG. 13 is a schematic view showing the averaging of estimates of motion in the system of FIG. 1.

Strictly only two motion detection operations per tracking array are required. However, by performing multiple tracking operations over various parts of the image (not necessarily on the center line), greater confidence in the accuracy of the method can be obtained. For example, as shown in FIG. 13 a smooth, straight line fit can be used to obtain an average of multiple estimates of the component of motion being detected. In FIG. 13 the dashed arrows represent the fitted component of motion and the continuous arrows represent the actual measures of the component of motion. By taking an average of multiple measurements a more reliable estimate is obtained. This average can be used both with respect to the amplitude and to the angle of the motion component vectors.

Figure 14:
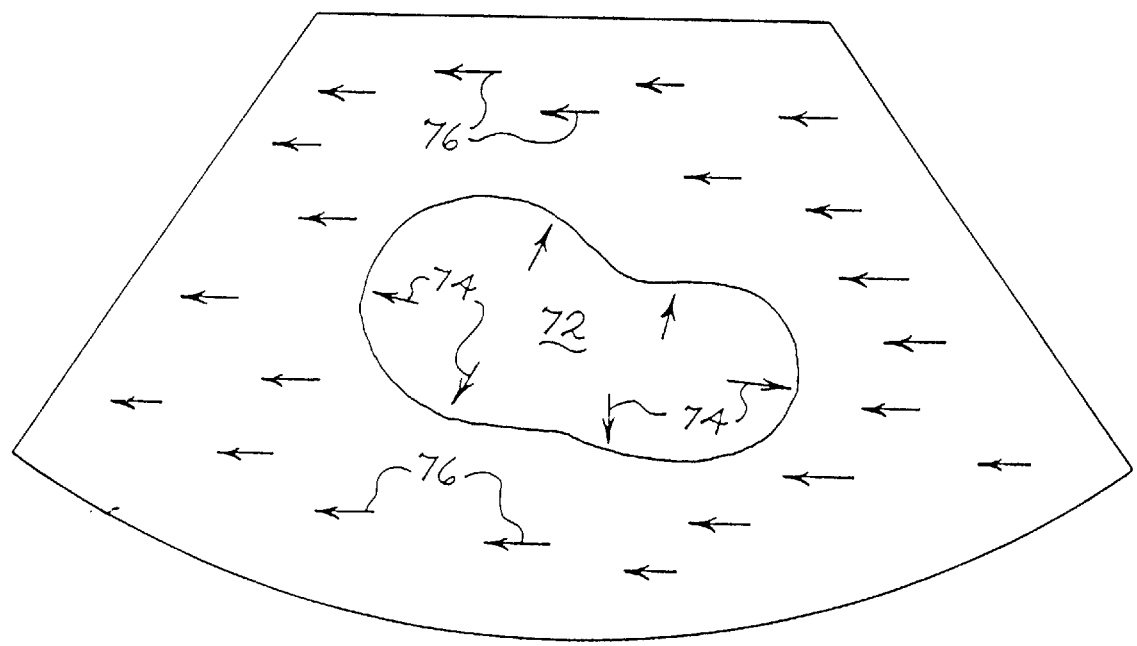
FIG. 14 is a schematic view showing how the bulk motion of an imaged organ can be recognized and disregarded in the system of FIG. 1.

Also, motion estimates which are radically different from neighboring estimates may be discarded as inaccurate. As shown in FIG. 14 an image of one of the tracking arrays can include an organ 72 having a bulk motion indicated by the arrows 74 which is different from the motion indicated by the speckle of the larger part of the area of the image. In this case the bulk motion of the organ can be disregarded, and the average of the remaining estimates of motion indicated by the shorter arrows 76 can be used as an estimate of the motion of the frame. One suitable approach is to quantize the motion vectors (length and direction), and then to find the most commonly occurring quantized length and direction. Next the actual (unquantized) vectors within a tolerance band (e.g. ±30%) of the most commonly occurring values are selected and averaged to generate the desired estimate.

Additionally, in a sum of absolute differences calculation, the ratio of the minimum sum to the average sum (after removing the minimum sum value) can be used as an indicator of the quality of the image motion detection. If the minimum sum is close to the average, then the calculation is susceptible to error, i.e. falsely detected motion. When the LSI 64720 integrated circuit is used, the sum of the error values output is an indicator of a low quality result (a high error value sum corresponds to a low quality result).

Low quality tracking may also be detected by comparing estimates of motion. Adjacent or successive estimates of motion which are not similar to one another may be an indication of low quality motion estimation. Of course, two or more of the approaches described above may be used in combination.

Speckle patterns change rapidly as motion occurs. In particular, a speckle pattern will change if the elevation slice position moves. This is because speckle scatterers move in and out of the image plane rather than remaining within the plane and moving parallel to it. For this reason it is preferable in many cases to make frequent motion estimates as the transducer 16 is moved. The exact frequency of the estimates will depend upon the scale of the motion detection problem, which is related to the speed of motion imposed by the operator, the operator's ability to maintain slice position, and the nature of the speckle target (which is a function of tissue type and ultrasound frequency).

By way of example, it may be determined that thirty image data frames from the image data array 18 provide sufficient imaging data for a desired 3-D reconstruction. However, it may be preferable to perform five motion estimates between each selected image data frame and to sum these estimates to calculate the net motion between the image data frames. Since cumulative errors are to be minimized, one way to achieve this result is to over-sample the motion detection operation and to average the results to reduce quantitation effects due to pixel size. With this approach there might be for example five frames from each of the tracking arrays 20, 22 for each frame of the image data array 18.

While motion detection often works best when performed from a sum of small motion detections, there are situations when it is of value to use motion detection between frame N and frame N-M, where M is a integer greater than 1, such as 10. In principle, this approach can be used to correct cumulative errors. However, the probability of such a large motion being correctly estimated is less. Therefore, the value of M is a matter for optimization.

Since elevation slice affects speckle quality and stability, it may be preferable to track motion at the elevation focus of the lens. Alternately, if the speckle dependence is too sensitive at the elevation focus, it may be preferable to avoid that area. It may be preferable to apply varying weightings to the detected motions during the smoothing operation to maximize the net accuracy by taking more account of more accurate data. It may be preferable to use an elevation focused array (1.5 D array) or perhaps an unfocused array if that appears during experimentation to provide the best results.

The data used for motion detection can taken many forms. Envelope-detected, scan converted data is a simple design choice, and is presently preferred. Alternatives include envelope-detected data prior to scan conversion and RF or baseband beamformer output signals prior to envelope detection.

It is also possible for the user to select regions of interest if for some reason the user has specific preferences about which regions in the tracking data image would provide the best motion detection. For example, a user may choose not to use volumes of moving blood as regions for motion detection.

During the collection of image data the preferred display is as shown in FIG. 20. In FIG. 20 an image from the image data array 18 is shown centrally on the screen and tracking images from the tracking arrays 20, 22 are shown on respective sides of the screen. Preferably, motion detection is performed in real time, and the detected motion is presented on the display by indicating the calculated motion as it occurs in real time. This display can take the form of motion vectors as shown in FIG. 20. Alternatively numeric measures of detected motion can be displayed. These displays indicate the relative position of the transducer in the sweep, and therefore provide the operator with an indication as to when the desired angular motion has been completed and also provide an indication of whether the motion detection system is working properly. Alternately, the image data may be displayed without the tracking images or without display of the detected motion. In the event that the system-calculated motion vectors indicate low-quality tracking (such as erratic changes in the calculated motion vector within a single frame or between successive frames) the system can prompt the operator to begin again, as for example with an audio prompt such as an alarm or a visual prompt such as a flashing, reverse video message.

If desired, the system 10 can be programmed to assist the user in achieving an optimum sweep rate. In many cases, optimum use of the motion estimators calls for an optimized sweep rate, i.e., a sweep rate that is large enough to avoid unacceptable error accumulation and small enough to remain within the range of movement of the motion estimator. Either an audio or a video prompt may be used.

For example, when the motion estimator is adapted to detect ±8 pixel motions, the system may emit an intermittent tone when the sweep rate is approximately correct (e.g., 4 pixels of movement per estimate). If the estimated movements are too small (e.g., less than 2 pixels), the intermittent tone is replaced with a low continuous tone, which becomes even lower if the sweep rate slows further. Conversely, if the estimated movements are too large (e.g., greater than 6 pixels), the intermittent tone is replaced with a high continuous tone, which becomes even higher if the sweep rate speeds up.

A suitable visual prompt includes a variable-length arrow, which can have a longer length to prompt a faster sweep rate and a shorter length to prompt a slower sweep rate, and which can flash to indicate an optimum sweep rate.

Another approach is to program the motion estimator to select the spacing in time of the frames that are correlated to estimate the component of motion. By properly selecting this spacing in an adaptive manner, the measured component of motion can be kept within the optimum range for a wide range of sweep velocities. For example, if there are many non-used tracking frames between each pair of correlated tracking frames, and if 8 pixels is the maximum detectable motion, the number of non-used tracking frames between each pair of correlated tracking frames can be increased or decreased as necessary in real time to maintain the detected motion in the range of 4 to 6 pixels.

Low quality motion estimates can be weighted at a low level or entirely removed. One approach for selecting low quality motion estimates is first to fit a curve to all of the motion estimates (both in length and angle). Then the individual motion estimates are compared to the fitted curve, and motion estimates that deviate from the curve by more than a threshold amount such as 30% are considered low quality motion estimates and are deleted from the collection of motion estimates. Then the curve fitting operation is repeated using only the remaining motion estimates. If more than a certain fraction such as 20% of the motion estimates are classified as low quality estimates, the operation can be abandoned and the user prompted to repeat the sweep.

Figure 12:
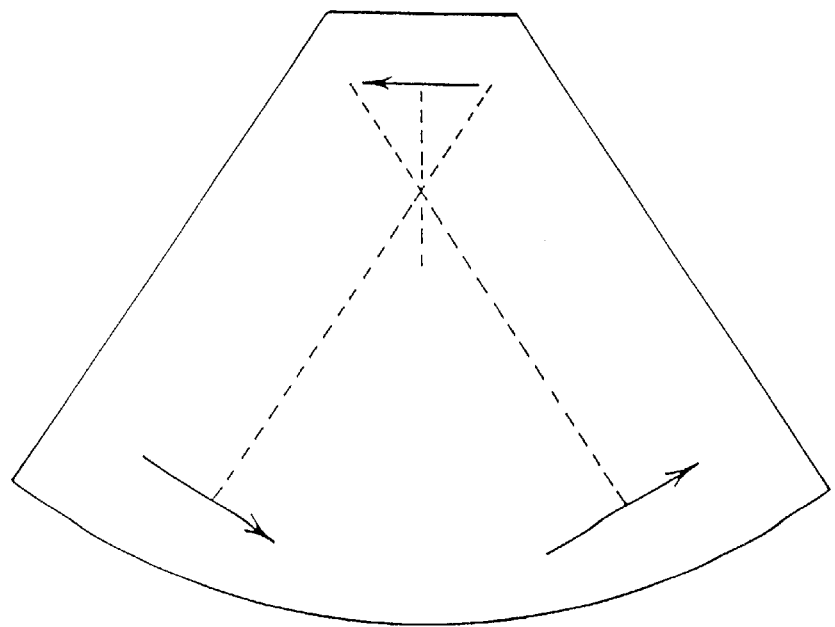
FIG. 12 is a schematic plan view of a tracking image region generated with the system of FIG. 1.

In general, it is often necessary only to determine the component of motion relating the relative positions of successive images. If required, it is also possible to determine the axis of rotation by drawing lines perpendicular to the determined motion vectors, as shown in FIG. 12. When this is done the length of the motion vector is an indication of the distance of the motion vector from the axis of rotation.

Strictly speaking, it is not necessary to have two tracking arrays 20, 22. However, when two tracking arrays are used, the ability to deal with impure rotation (where one end of the image data array 18 is rotated more than the other) is substantially increased. Furthermore, when multiple tracking arrays are used and motions for various ranges on each tracking array have been determined, interpolation may be applied to find the center of rotation that applies for all intermediate points in the range direction on each tracking array.

Since the tracking arrays are on either side of the image data plane, and the exact geometry of the image data plane with respect to the tracking arrays is known, it is possible to interpolate linearly along the image data array azimuth axis to calculate the exact pixel translations for all points on the image data plane.

Typically, motion estimates are collected along a straight line or across a rectangular grid. Due to the constraints of the array geometry and the propagation of the straight acoustic lines from the array, the theoretical behavior of the motion vectors as a function of depth must satisfy certain constraints. In particular, the lengths of the motion vectors should vary linearly with depth. These constraints can be used to reduce the error in the estimated motion. For example, a sequence of motion estimates can be acquired as a function of depth and then converted to motion estimate vectors (length and angle). A straight line is then fitted using well known methods to determine the best fitting line to the actual data for the length component. A second straight line is then fitted to the actual data for the angle or direction component. These fitted lines (comprising length and direction) can be linearly interpolated along the azimuthal direction during three-dimensional reconstruction at intermediate locations other than those used to derive the motion vectors.

Note that if the patient and the transducer 16 move slowly together, loss of performance is not necessarily the result, as long as the relative position of the transducer 16 with respect to the patient is largely maintained.

In order further to improve motion estimation it may be desirable to utilize only images corresponding to selected portions of the ECG cycle or the breathing cycle. Both ECG gating and breathing gating are well known in three-dimensional reconstruction of images. See, for example, McCann et al. "Multidimensional Ultrasonic Imaging for Cardiology" at p. 1065. With ECG gating a window is selected a fixed time duration after the ECG pulse maximum. With breathing gating it is often simplest to ask the patient to hold his or her breath for the short duration of the ultrasonic scan. Alternatively, chest motion can be recorded using a displacement sensor, and data can be selected for a portion of the breathing cycle.

Various other techniques can be used to optimize motion estimation. For example, accuracy can be improved by interpolating to finer and finer pixels. Noise in the data can be removed using a low pass filter or a median filter, and the mapping of voltage level to brightness can be optimized for motion estimation purposes. Typically, logarithmic compression is used on the tracking arrays 20, 22, and this logarithmic compression can be optimized independently of the logarithmic compression used for the image data from the image data array 18. The particular mapping that is used can vary widely according to the operator's wishes. It is likely that in many cases motion detection will function most efficiently using a different mapping than that used by the operator for the image data. If desired, the system 10 can vary the mapping used internally for the data from the tracking arrays 20,22 until a mapping is found that provides high quality motion detection.

Three-Dimensional Volume Filling Computer 36

Many approaches can be taken in aligning the image data frames to provide the desired three-dimensional reconstruction. One example is shown schematically in FIGS. 17–19. In this example, the image data frames prior to reconstruction are shown schematically in FIG. 17. The image data frame for the central plane is inserted at a plane aligned with the center of the volume, as shown in FIG. 18. Working outwardly from this center plane, successive image data frames are inserted into their appropriate XYZ locations, as shown in FIG. 19. Once all frames have been inserted, intermediate points are calculated using three-dimensional linear interpolation techniques relying on the eight closest known data points, arranged as a cuboid around the point to be interpolated. Such three-dimensional manipulation techniques are known, and are therefore not described in detail here.

One approach is to use the scan conversion interpolation method described by Leavitt in Hewlett Packard Journal, October, 1983, pp. 30–34, adapted for use in three dimensions. The approach described by Leavitt operates with data in a two-dimensional plane. Data in three dimensions can be treated in two successive two-dimensional operations. Image plane data can be scan converted and interpolated as described by Leavitt, using pixel spacings that match the requirements of the three-dimension scan conversion. Then an orthogonal two-dimensional scan conversion can be performed at each azimuthal position to fill out the volume in the perpendicular direction. The Leavitt technique assumes that the axis of rotation for successive two-dimensional images is correctly aligned. If this is not the case, other volumetric reconstruction methods can be used. Suitable reconstruction methods are well-known and are used with conventional magnetic sensor-based systems.

If successive frames are detected to be too close together, some of the frame data may be discarded. If there are a large number of frames, it is, possible to keep only those which happen to be spaced close to some desired uniform spacing. For example, if the desired spacing for reconstruction is 2° and data is acquired at 0, 1.2, 2.1, 2.8, 3.9 degrees, then frames 1, 3 and 5 can be approximately assumed to be the correct frames lying at approximately 0, 2, and 4 degrees. The error from the approximation is insignificant and may result in simplicity in the reconstruction.

Translation Detection Techniques

It should be noted that a component of motion within the image data frame can also be detected using the techniques discussed above. This component of motion will be parallel to the azimuthal axis, and can be added to the motion detected with the tracking arrays, which is perpendicular to the azimuthal axis. Since the image data from the image data array 18 will move significantly due to motion of the elevation plane, it is preferred that motion detection be over-sampled in this plane. Preferably, only a measured net motion is applied during the reconstruction, as discussed above in conjunction with FIG. 14.

Also, motion can be detected in the plane of the image data frame when the transducer 18 is moved in translation along the azimuthal axis, as opposed to the rotational sweeps discussed above. With this approach, an extended field of view can be provided by axially shifting the transducer 16 along the azimuthal axis, without rotating the transducer 16. If the only interest is in tracking such linear translation, the tracking arrays 20, 22 are not required.

As used herein, extended field of view denotes a system which stores image data from a transducer array as the transducer array is shifted axially along its azimuthal axis. Data from the array at various positions along the azimuthal axis are then registered for reconstruction to form an extended field of view image.

The extended field of view discussed above can be reconstructed with data from either one of the tracking arrays 20, 22 or the image data array 18. More logically, the image data array 18 is used, because the image data array 18 is optimized for image quality. The image data array is then translated with respect to the target tissue, with its azimuthal axis oriented parallel to the line of motion. Image motion detection using the techniques described above is performed on image data from the image data array 18. Successive frames of image data from the array 18 are stored, along with displacement information defining the motion between frames of image data.

Once the sweep of image frames has been completed, the displacement information is used, starting with the most recently acquired image data frame, to register successive ones of the image data frames with respect to one another in proper alignment, in the tissue sense. The older image data is then superimposed on the newer image data. Typically, most of the older data will almost exactly match the newer data, but a small non-overlapping region will be present which represents data acquired at the older image position which could not be acquired at the newer image position. Preferably, during the writing of the older data over the newer data, only the non-overlapping region is written. This approach eliminates redundant image writing operations. This procedure is then continued for progressively earlier frames of image data until all of the frames in the sweep have been reassembled for display.

There is a potential that attempts may be made to write beyond the limits of memory. If this situation is detected the image data can be scaled to make it smaller to fit into the available screen memory. Scaling may be achieved by remapping the pixels to a new memory using geometric transformation and interpolation, as is well known in the computer graphics field.

The following methods can be used either alone or in various subcombinations to enhance motion detection.

1. Frequency selection. In one example, every Nth frame is used for motion detection. On every Nth frame a different frequency is used to excite the transducer elements of the image data array 18 in order to modify the speckle pattern in such a way as to enhance the capability to detect motion. Since only relative motion is required, it may be preferable to use a higher frequency to obtain higher resolution speckle data at every Nth frame. Higher frequencies are associated with reduced penetration depths, but as discussed above this may not be a drawback since only shallow target data may be required for motion detection. Alternately, higher frequencies may make speckle highly position sensitive. This may be undesirable if it causes the motion detection operation to fail due to an inability to track features that move in and out of the elevation plane of the image. In this case, it may be preferable to use a lower frequency for the motion detection frames.

2. Bandwidth adjustment. As above, selected ones of the image data frames may be optimized for motion detection, in this case by optimizing the bandwidth as well as or instead of the center frequency for motion detection.

3. Elevation focusing. When a 1.5 dimension array is used, elevation focusing can be adjusted during the sweep to optimize some frames for image data collection and other frames for motion detection. For example, to reduce the impact of elevational motion, it may be preferable to defocus the beam slightly in those image data frames used for motion detection.

4. Azimuthal focusing. Similarly, it may be preferable to defocus the acoustic beam slightly in azimuth for selected frames to stabilize motion detection without degrading motion detection excessively.

When any of the four approaches discussed above are used, the image data frames that are optimized for motion detection need not be displayed on the screen. Instead, only the image data frames that are optimized for imaging can be used.

Since during a slow sweep there is redundant data (multiple data points for individual positions within the tissue), it may be preferable to mix the use of different frequencies, bandwidths and focusing methods to collect redundant motion detection data. After multiple redundant data is collected, it can be averaged to arrive at a motion estimate which is more reliable and less vulnerable to error.

By way of example, if the array is moved at two millimeters per second, the required minimum motion which can be usefully resolved is 0.5 millimeters, and the frame rate is forty frames per second, there will be ten frames between times when useful motion detection can be obtained. Also, we need only one image data frame for each of these ten motion detection frames. If we consider the first twenty frames, frames 1 and 11 can be image data collected using user- determined center frequency and bandwidths. Frames 3 and 13 can be motion detection frames with first alternative center frequency and bandwidth. Frames 5 and 15 can be motion detection frames with second alternative center frequency and bandwidth, and frames 7 and 17 can be motion detection frames with the first alternative center frequency and the second alternative bandwidth. Frames 9 and 19 can be motion detection frames using a changed focusing scheme. Frames 2, 4, 6, 8, 10, 12, 14, 16, 18 and 20 are captured as if they were image frames and are displayed, but are not stored or used for tracking. The detected motion from frames 1, 3, 5, 7 and 9 with respect to frames 11, 13, 15, 17 and 19, respectively, may then be averaged or sorted so as to eliminate motion estimates which are significantly different from other estimates.

All of the techniques described above in connection with extended fields of view can be adapted for use with motion detection in angular sweeps as described above.

In the case of a complex motion involving motion in both the planes of the tracking arrays and motion in the plane of the image data array, the actual motion may be calculated approximately from the sum of the tracking array motions and the image data array motions, separately measured. If after the sum of such motions is obtained it is found that the second motion to be applied has caused the first motion to have been modified, a recursive operation can be employed until a three-dimensional motion is found which correctly satisfies the detected motions in all arrays. A Monte-Carlo method for finding the components satisfying a complex motion may be used. Additionally, new motions may be estimated from the last frame-to-frame motion which was calculated. As a last resort, the system can find that it is unable to determine a set of motion component vectors which satisfy the detected motions and can signal the operator to repeat the last sweep. The simpler, smoother, and purer that image movement is in any given image plane, the easier it is to implement motion detection.

Alternative Embodiments

A simpler device for implementing the bi-plane imaging techniques discussed above can be constructed as follows. This device also uses a linear array for the image data acquisition and two small linear arrays of equal pitch that are mounted to move with the larger linear array. The two small linear tracking arrays are coupled to a connector similar to that used by the image data array, but the transducer elements are divided so that the transducer elements for each tracking array are coupled to the transducer connector near the opposite ends of the connector. For example, for a 128 conductor connector and a 10 element tracking array, the conductors 10–19 and 100–109 can be used for the two tracking arrays. Both the image data array and the combined tracking array are provided with a connector of the same type and are designed to operate with the same beamformer. The two connectors are inserted into the left and right ports of a suitable ultrasonic imaging machine, such as the Acuson Model XP, and an image storage device such as a VCR is provided. As the array is rotated slowly the operator presses the array select switch (left versus right) repeatedly at a high rate and the resulting images are stored for off-line analysis. At the end of the sweep, the VCR tape is played back on a frame-by-frame basis. Successive sets of frames, each set consisting of a frame from the image data plane and each tracking image plane, are transferred via standard video transfer techniques to a computer memory. The computer is programmed to analyze the tracking image plane data for motion detection using the methods discussed above. The tracking image will in fact appear as two images, one on each side corresponding to the two spatially separated tracking arrays. The two images are analyzed separately.

As a preferred modification to the simplified system described immediately above, the ultrasonic imaging machine is preferably programmed to perform the array switching operation and to transfer one set of frames from each sequential sweep to computer memory or to a suitable storage device.

Alternative Transducers

Many variations are possible on the preferred transducers described above. For example, crossed arrays of the type described in Hashimoto U.S. Pat. No. 5,327,895 and Schaulov, et al., Ultrasonics Symposium, pp. 635–638 (IEEE, 1988) can be adapted for use with this invention. Such crossed arrays typically include a PZT plate which is diced in perpendicular directions. The kerfs are filled with a low-durometer polymer such as a low-durometer epoxy. Linear electrodes (defining the array elements) are applied to the top and bottom surfaces, and the electrodes on the top surface are oriented perpendicularly to the electrodes on the bottom surface. When using the array in one direction, all electrodes on the top surface are grounded and the electrodes on the bottom surface are excited with the phased excitation pulses. The electrodes on the bottom surface are then monitored for detected echoes. When using the array for the other direction, the bottom surface electrodes are grounded and the top surface electrodes are operated in a phased manner.

Both arrays in a crossed array configuration may be used simultaneously. For example, one array may be operated using a different center ultrasonic frequency than the other. Also, both arrays may be used independently of one another, as indicated by the principle of voltage superposition, thereby accommodating simultaneous operation of both arrays.

FIGS. 23–26 show schematic views of four crossed arrays that can be used to collect both image data and tracking information. In the transducer 100 of FIG. 23 the elements 102 form a conventional one-dimensional array that can be used to collect image data. Crossed elements 104 at both ends of the transducer 100 can be operated as tracking arrays as described above. The transducer 100' is similar to the transducer 100 except that the crossed elements 104' are provided only at one end.

The crossed array 100" of FIG. 25 is also similar to the array 100 of FIG. 23, except that the crossed elements 104" are provided only at the center of the transducer. FIG. 26 shows a transducer 100''' which is similar to the transducer 100'' of FIG. 25, except that the crossed elements 104''' extend over the entire length of the array.

As shown in FIGS. 23–26, one or more tracking arrays can be integrated with an image data array using the crossed array technique. The crossed array is operated in the normal manner along the long, azimuthal axis to obtain 2-D image data. The crossed arrays are operated to obtain data along the elevation direction to obtain the perpendicular tracking data. In this way the footprint of the transducer is minimized. If desired, the tracking data may be acquired from the same volume of tissue as that being interrogated to obtain the image data.

FIG. 27 provides a schematic view of another transducer 110 which includes an image data array 112 and a single tracking array 114. In this case the tracking array 114 is oriented perpendicularly to the image data array 112. As shown in FIG. 27 the tracking array 114 is laterally offset from and centered with respect to the image data array 112.

FIGS. 27a through 27e show five alternative transducers, each including a single image data array 112 and at least one tracking array 114. In the transducer of FIG. 27a there are two tracking arrays 114, both laterally offset from and centered with respect to the image data array 112. In the transducer of FIG. 27b there is a single tracking array 114 that is co-linear with and axially spaced from the image data array 112.

The transducer of FIG. 27c includes two tracking arrays 114, both positioned to the same side of the image data array 112 near opposite ends of the image data array 112. The transducer of FIG. 27d is similar to that of FIG. 27c, except that the two tracking arrays 114 are positioned on opposite sides of the image data array 112. The transducer of FIG. 27e includes four tracking arrays 114, two on each side of the image data array 112, near respective ends of the image data array 112.

Figure 27F:
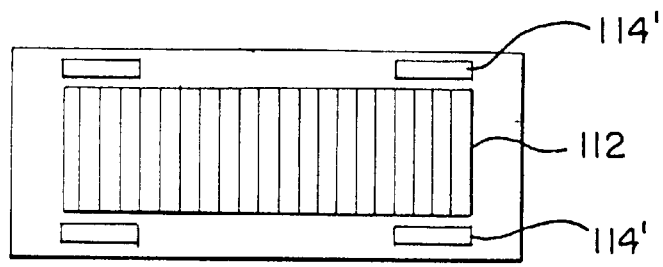

FIGS. 27f through 27j show additional transducers that can be used with this invention, each including a single image data array 112 and at least one tracking array. In the transducer of FIG. 27f, each tracking array includes two single-element transducers 114'. Each of the tracking arrays is situated near a respective end of the image data array 112, and the individual single-element transducers 114' are elongated elements oriented generally parallel to the azimuthal axis of the image data array 112. The two single-element transducers 114' in each tracking array can be operated as an interferometric, two-element transducer array. The single-element transducers 114' can be fired using a narrow-band transmit signal, for example either in phase or 180° out of phase. Receive signals generated by the two single-element transducer elements 114' can then be added together to create a summation signal. Consecutive summation signals can then be compared to one another with various offset delays. The offset delay which gives the best correlation (in a least squares sense for example) is a function of the motion of the transducer between the respective firings of the transducers 114'. Using this best correlation time delay, and taking into account the sound propagation velocity through the two way path, one can then determine the associated physical displacement of the transducer between the associated firings, as described in detail above.

The comparison operation may be performed in either the time or the frequency domain. If the frequency domain is used, complex values or phase values are preferably compared. For many applications a time domain comparison will be simpler. Because the two single-element transducer elements 114' within a single tracking array are relatively widely spaced, they provide the benefit of relatively good lateral resolution. High grating lobes will typically be associated with this configuration, but it is envigaged that high side lobe levels will be less objectionable for use in an automated tracking algorithm than for use in a gray scale display intended for human interpretation.

In some applications the method described above would principally detect motion parallel to the beam axis. In these cases it may be preferable to form the beams with a substantial component in the direction of the expected motion. Since motion is principally in the lateral direction (transverse to the azimuthal axis of the image data array 112), one option is to form the beams at +/−45° or +/−60° from the central image plane of the image data array 112.

Figure 27G:
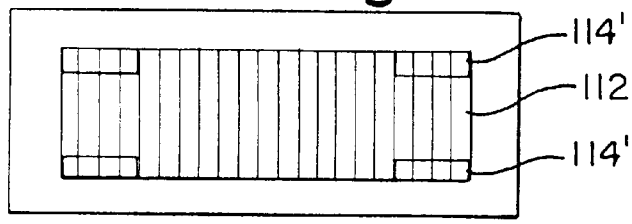

As shown in FIG. 27g, the single-element transducer elements 114' may be superimposed on the image data array 112. This can be done using crossed arrays as described above, or by placing one of the arrays physically over the other. In this case the upper array should be as nearly transparent as possible with respect to ultrasonic radiation emitted by the lower array. In the example of FIG. 27g the image data array 112 may be an elongated, one-dimensional, ceramic-based array, and the single-element transducer elements 114' may comprise PVDF arrays mounted with perpendicularly-oriented elements on top of the image data array. In fact, the PVDF tracking array may perform the function of a matching layer for the image data array. A non-conducting plastic film may be placed between the superimposed arrays to prevent cross talk or shorting.

Figure 27H:
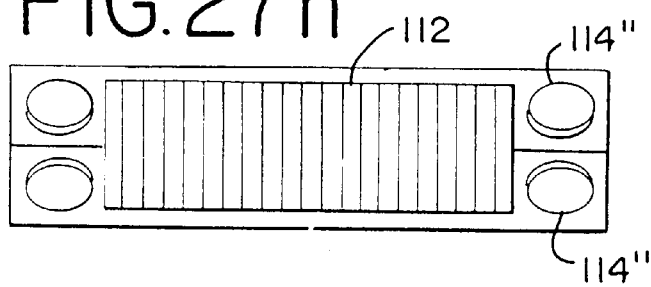
Figure 27I:
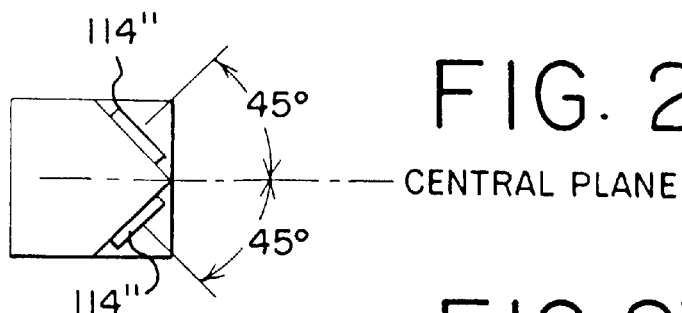
FIG. 27i is an end view taken along line 27i–27i of FIG. 27h.

As shown in FIGS. 27h and 27i, the single-element transducer elements 114'' may take the form of circular elements which may be preferably focused at some range, as for example 40 millimeters. In this case, the receive signal generated by a single one of the single-element transducer elements 114'' is compared with subsequent firings of the same single-element transducer element, and beamforming operations are eliminated. In this case, each individual one of the single-element transducer elements 114'' acts as a respective tracking array, and the term "tracking array" is intended broadly to encompass such single-element arrays.

Figure 27J:
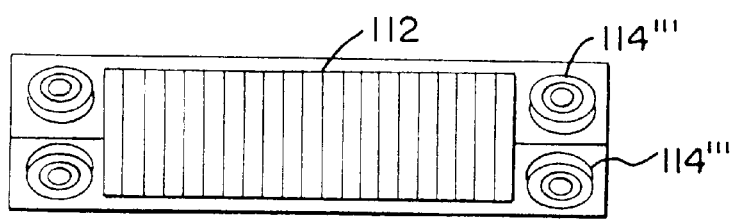

As shown in FIG. 27j, each individual tracking array 114''' may take the form of an annular array. Annular arrays are well known for use in mechanically scanned transducers, and they provide the advantage that they can be focused in transmit and dynamically focused in receive to produce a high quality beam profile. Each annular array 114''' is typically composed of cross-diced PZT ceramic with an epoxy filler. Chromium/gold spatter electrodes are applied to the PZT ceramic, and these electrodes are etched selectively (or mechanically scribed) to isolate approximately 8 discrete electrodes on one side. The reverse side has a continuous metalized layer and is grounded. As described above, the tracking arrays 114''' may be oriented at ±45° or ±60° for example with respect to the central plane of the image data array 112. A low loss, non-refractive filler polyurethane such as the resin distributed by Ciba-Geigy as resin no. RP6400 or other suitable diphenylmethane diisocyanate polyurethane can be used to fill the space between the transducer elements 114''' and patient tissue.

Transducer geometries that place the tracking arrays alongside the image data array may reduce the overall length of the transducer, which may provide advantages in some applications.

As shown in FIGS. 28 and 29, a transducer 120, 120' suitable for use in forming an extended field of view as described above can utilize an image data array 122 and a tracking array 124, wherein the transducer elements of the two arrays 122, 124 are parallel to one another. In the transducer 120 the tracking array 124 is laterally offset from and centered with respect to the image data array 122. As shown in FIG. 29, in the transducer 120' the image data array 122' and the tracking array 124' are collinear and separated from one another. With either of the transducers 120, 120' frame-to-frame motion can be determined using the tracking arrays 124, 124' and the compound image can be assembled from image data from the image data array 122, 122'.

In any of the foregoing embodiments, some or all of the tracking arrays and the image data arrays may be formed as non-planar linear arrays such as curved linear arrays for example. Separate, oriented linear arrays may be used for each acoustic line if desired.

Alternative Optimization Techniques for Tracking Data

Figure 30A:
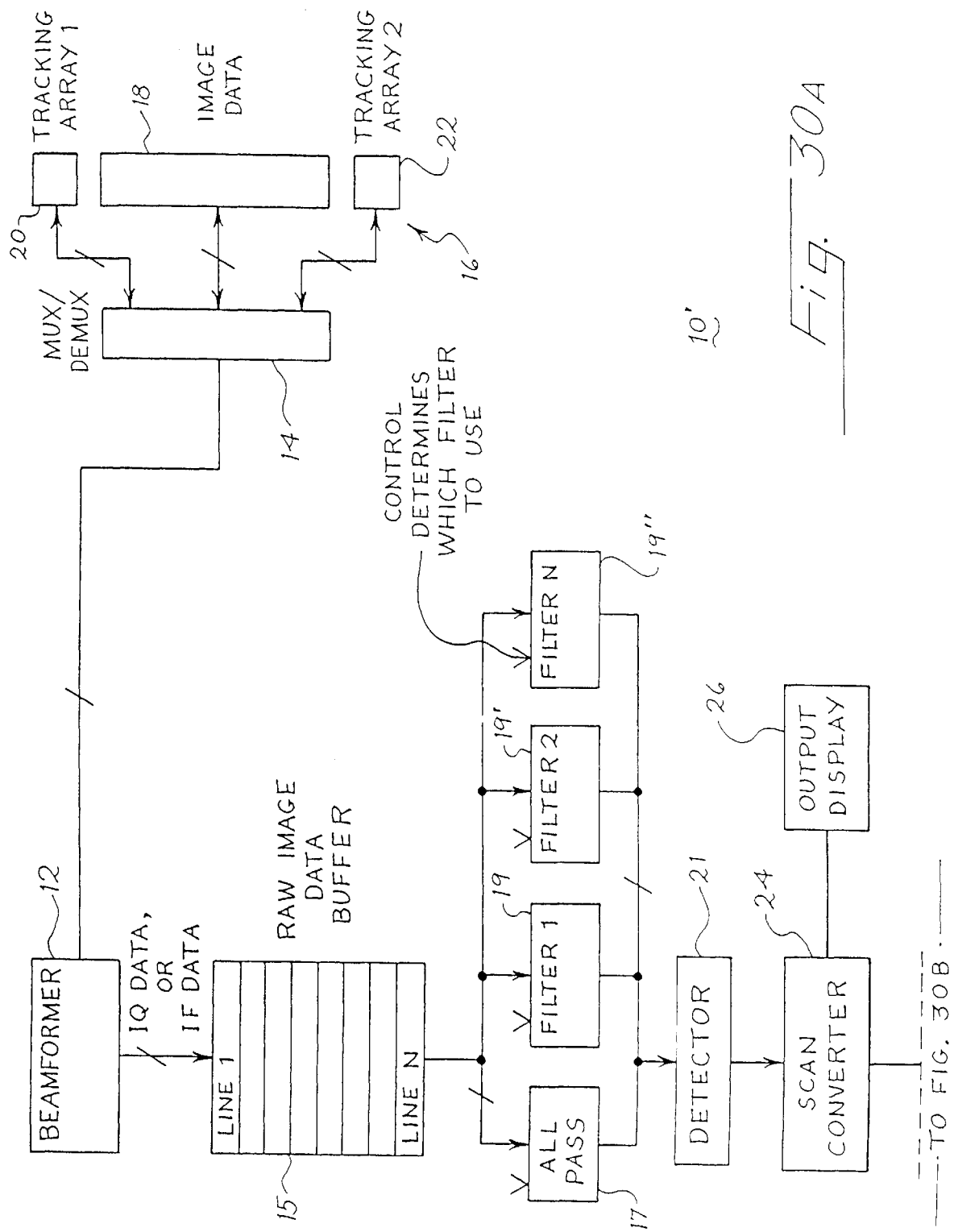
FIG. 30 is a block diagram of an ultrasonic imaging system which incorporates a preferred embodiment of this invention.

FIG. 30 is a block diagram of an alternative ultrasonic imaging system 10' that is in many ways similar to the system 10 of FIG. 1. The same reference numerals have been used for comparable elements in the two drawings, and the following discussion will focus on the differences. The system 10' stores image data from the image data array 18 or one of the tracking arrays 20, 22 in a raw image data buffer 15. The data stored in the buffer 15 can be I, Q data or IF data, for example. Of course, the term "image information" is intended to refer broadly to information that varies with spatial variations in the target, and in many cases image information is never displayed as an image. Preferably, the raw image data stored in the buffer 15 includes tracking data stored with wide band ultrasound pulse operation. Image data from the buffer 15 is passed to a detector 21 through one of four alternative blocks. Block 17 is an all-pass block which performs no filtering, and which is typically used for image data from the image data array 18. Tracking data from one of the tracking arrays 20, 22 can be passed through one of three filters 19, 19', 19", which can have varying filter characteristics. For example, filter 19 may be a low-pass filter and filter 19' may be a high-pass filter. Filter 19" may be a band-pass filter centered in any desired portion of the frequency spectrum.

The detector 21 can be any conventional detector, and it supplies a detected output signal to the scan converter 24. If desired, tracking data from the tracking arrays 20, 22 can be processed multiple times, using different ones of the filters 19, 19', 19". Of course, more or fewer filters can be used in alternative embodiments.

The scan converter 24 preferably uses the well-known histogram equalization method to maximize contrast in the tracking image data. Histogram equalization is discussed for example in Gonzales and Woods, *Digital Image Processing*, Addison-Wesley, 1993, pp. 173–178, as well as in Kim U.S. Pat. No. 5,492,125. The scan converter 24 may use a 2 D low-pass filter and/or a 2 D high-pass filter to smooth or otherwise process the tracking image data.

Image frames from the scan converter 24 are stored in the frame buffers 30, 32, 34, and tracking sets of image data from the buffers 32, 34 are selectively applied to the motion estimator 38. The motion estimator 38 estimates the relative motion between selected tracking image sets and applies these estimates of motion to a motion smoothing/summing block 40'.

The motion smoothing/summing block 40' processes motion estimates from multiple motion detection operations. Preferably, each motion detection estimate is associated with a quality factor indicative of the confidence level associated with the motion estimate. For example, a suitable quality factor may be value of the minimum sum of absolute differences associated with a particular motion estimate. The block 40' compounds multiple motion estimates using a weighted sum. For example, consider the situation where three motion estimates are available with the following values and associated quality factors Q:

Estimate 1—5 Pixels to the right Q=0.9
Estimate 2—3 Pixels to the right Q=0.8
Estimate 3—2 Pixels to the left Q=0.2

In this example, a high value of Q is associated with a high confidence level. The block 40' can form a weighted sum of these three motion estimates as follows:

$$\text{Motion Estimate} = \frac{(5 \times 0.9) + (3 \times 0.8) + (-2 \times 2.0)}{(0.9 + 0.8 + 2.0)}$$

$$= 3.4 \text{ Pixels to the right.}$$

The previous motion store 41 FIG. 3 is used to store previous motion estimates until they are needed in forming the weighted sum described above. Other methods for using multiple motion estimates are described below.

Other techniques that can be used to improve the quality of the motion estimate include the use of multiple transmit zones to acquire the best quality tracking image data and the use of a frequency-dependent focus as described in Hossack U.S. Pat. No. 5,608,690, assigned to the assignee of the present invention, to acquire the best quality tracking image data.

As pointed out above, the acquisition of image data via the array 18 can be time multiplexed with the acquisition of tracking data via the tracking arrays 20, 22. In one alternative embodiment the time separation between consecutive tracking data frames is controlled adaptively to provide motion estimates that fall within a desired range. As explained above, if the motion estimate (i.e. displacement) between consecutive tracking frames is excessive, there is a danger that the displacement may exceed the measuring capabilities of the motion estimator 38. Conversely, if the motion estimate between consecutive tracking frames is too low, excessive computational time may be used in creating motion estimates. Additionally, if the motion estimates are small, the relative errors will be large, and compound errors may reach undesirable proportions. In order the avoid these problems, a controller can be provided as described above to determine the number of image data frames that are collected between consecutive tracking frames, and this can be accomplished in an adaptive manner as shown in FIG. 31.

Figure 31:
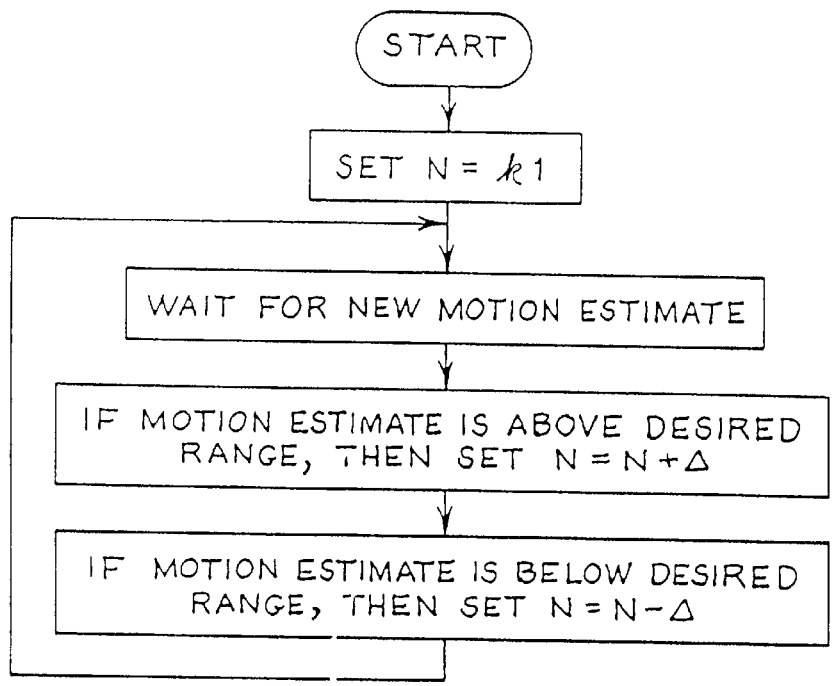
FIGS. 31 and 32 are flowcharts of routines performed by the imaging system of FIG. 30.

In FIG. 31 the variable N is used to specify the number of image data frames that are collected between consecutive tracking frames. As shown FIG. 31, N is initially set to a constant K1, and the controller then waits for a new motion estimate from the motion estimator 38 of FIG. 3. If this motion estimate is above a desired range, than N is reduced by the amount Δ. Conversely, if the motion estimate is below the desired range than N is increased by Δ. Once N has been revised if necessary, the controller then waits for a new motion estimate from the motion estimator 38. In this way the motion estimate is maintained within a desired range automatically, and problems associated with excessively large motion estimates or excessively small motion estimates are avoided.

Image Transfer Optimization Techniques

The system 10' of FIG. 30 is well-suited for use in situations where a remote computer is used to perform motion estimation, either in real time or after a delay. In this context remote may mean that the motion estimating computer is connected via a cable or other data link. As shown in FIG. 30 image data frames from the buffer 30 can be compressed using any suitable compression technique such as JPEG prior to transfer to the potentially remote site. After the image data has been received at the potentially remote site, it is decompressed as shown in block 35. Similar compression and decompression blocks can be interposed between the buffers 32, 34 and the motion estimator 38. For example, remote motion estimation and 3 D volume reconstruction can be performed on a remote workstation such as the AEGIS workstation of Acuson Corporation, the assignee of the present invention.

Alternative Motion Estimation Techniques

Figure 32:
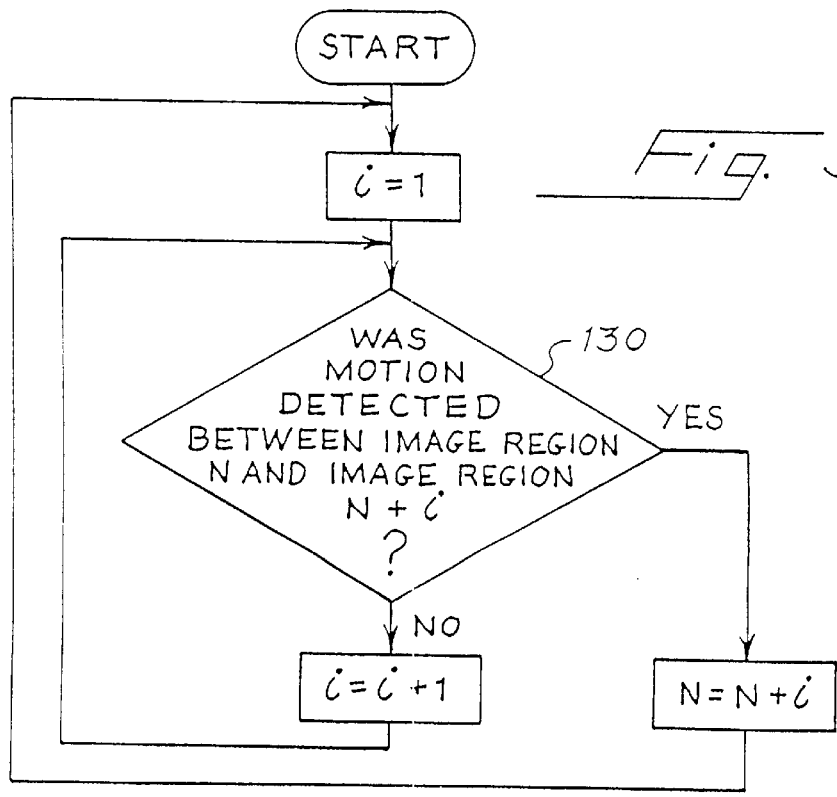

In the event that motion between consecutive tracking frames is small (less than one pixel) there is a danger that motion may be mis-estimated if each tracking frame is compared with the immediately preceding tracking frame. For example, if the separation between adjacent tracking frames were ⅓ of a pixel, the comparison of each tracking frame with the immediately preceding tracking frame would detect no motion. In order to overcome this problem, the motion estimator 32 of FIG. 30 preferably is controlled using the algorithm of FIG. 32. In this algorithm, N defines the frame number of the image region used as a reference in estimating motion, and the symbol N+i is used to designate the frame number of the image region that is to be compared with the reference image region, As shown in FIG. 32 the first step is to set i=1 and then to determine whether motion was detected between image region N and image region N+i. If not, i is incremented and control is returned to block 130. Once motion is detected in block 130, the reference image frame is updated to equal N+i, i is reset to 1, and control is returned to block 130.

For example, consider a sequence of tracking frames 1, 2, 3 and 4. Assuming no motion is detected between frames 1 and 2, then frame 3 will be compared with frame 1. Assuming no motion is detected between frame 3 and frame 1, then frame 4 will also be compared with frame 1. This process is repeated until motion is detected, and it is only then that the reference frame is updated to the new frame at which motion was detected. In this way, multiple subpixel motions do not go undetected, because subpixel motions eventually sum to the point where they become detectable.

The selection of the reference image region does not necessarily correspond to an entire frame. If frame motion is zero at the top and non-zero at the bottom of the frame (as might be the case with a fan-like sweep), then the older frame portion is preferably kept as the reference for motion detection at the top of the frame, while the bottom of the frame is updated once motion is detected in that region.

Since the tracking arrays 20, 22 are principally swept along the surface, the majority of motion will be in the elevation direction rather than the depth direction. During the search for the minimum sum of absolute differences (MSAD), it is preferable to make the search region rectangular rather than square. For example, instead of searching an area 64×64 pixels, a 128×32 pixel area can be searched in the same time (128 lateral search pixels and 32 depth search pixels). Similarly, if the maximum motion is 64 pixels, then by limiting the area of the search to 32×64 pixels, the search time is greatly reduced.

Additionally, frame motion can be interpolated to further reduce processing time. For example, if tracking frames 1, 3 and 5 are used for motion detection (rather than 1, 2, 3, 4 and 5), then detected motion between frames 1 and 3 can be interpolated to determine the motion for frame 2. In this case the interpolated motion for frame 2 would be one-half of the detected motion between frames 1 and 3. This method allows reduced processing time to be spent for motion detection, but allows all acquired image data to be employed in the highest quality 3D image. Interpolation of this type may be performed in the 3D volume translation/interpolation block 36 of FIG. 30.

Various alternative approaches can be used in the motion estimator 38 to further reduce processing time. For example, if a small set of acoustic lines are transmitted, received and stored as one-dimensional RF or baseband signals, then vector components of motion along each of these lines can be estimated by correlating successive sample sequences along the lines. In this way the vector component of motion in each of the line directions can be determined, and these vector components of motion can be summed to create the final two-dimensional motion estimate. If desired more than two acoustic lines may be used in the set, but the following example uses two perpendicular acoustic lines.

Figure 33:
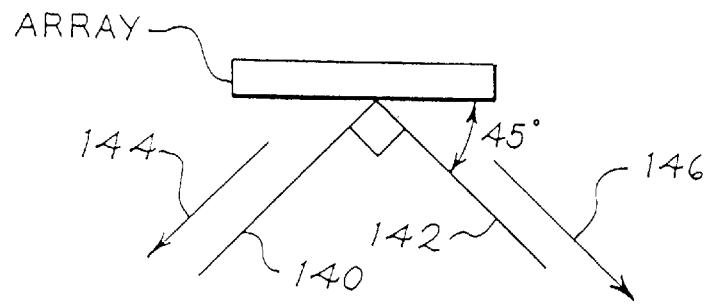
FIG. 33 is a schematic diagram illustrating operation of an alternative embodiment.

For example, as shown in FIG. 33, the tracking array 20 can be used to store two acoustic receive lines 140, 142 which are perpendicular to each other. These lines can be considered to make up a single frame of tracking data. The line 140 can be cross-correlated between two separate frames of tracking data to find the vector component of motion along the direction of the arrow 144, and similarly the lines 142 in these two frames of tracking data can be used to determine the vector component of motion in the direction of the arrow 146. These two components of motion can then be summed as vectors to estimate the two dimensional motion between the two frames of tracking data. Cross-correlation techniques suitable for adaptation to the current task are described in Engeler U.S. Pat. No. 4,937,775, O'Donnell U.S. Pat. No. 4,989,143 and Wright, et al. U.S. Pat. No. 5,570,691. The Wright, et al. patent is assigned to the assignee of the present invention.

Preferably, a register is used to store the complex sampled beam data from one firing in one of the two directions. When, an instant of time later, the same beam is formed again, the resulting sampled beam data is cross-correlated with the data in the register. From the position of the cross-correlation peak, the relative time delay between the two signals is determined. The cross-correlation process may operate on one or more portions of the available line data. By detecting motion via cross-correlation at a number of points along each line, separate motions can be determined at the top and bottom of the image, and hence rotations as well as translations can be estimated. From the time delay determined by the cross-correlation peak, the component of transducer motion (parallel to the beam axis) required to cause the measured time delay is inferred from the known speed of sound in tissue and taking account of the fact that the delay is related to two-way path length. This process is repeated for the other line (preferably oriented perpendicularly to the first line) to find the other vector component of motion. These two vector components are then summed to find the estimated actual transducer motion at that point along the array. Similarly, the process is typically repeated at the second side of the array for the second tracking array.

In one embodiment, the two lines (and therefore the two beams) are oriented at ±45 degrees, and there is therefore a strict requirement on element spacing if grating lobes are to be avoided. In another embodiment, the two lines are oriented at ±60 degrees to enhance the accuracy of motion detection along the skin of a patient. Preferably, the transducer elements should be spaced at one-half wavelength or less. This requirement may encourage the use of a lower frequency for the tracking arrays than for the image data array. However, it is possible that the cross-correlation technique will be able to track delay to a small fraction of a wavelength. As before, the comparison between one set of tracking data and the next may not be made on every acquired set of tracking data, but rather on a time-spaced subset. For example, if motion is fast, motion estimates can be made between every consecutive pair of sets of tracking data, but if motion is slow a longer time between motion estimates is allowed.

Fast Motion Detection Search Techniques

A variety of methods are available for speeding up the search for the estimated motions. These methods can be used with any of the embodiments described above.

1. Either the system controller or a user input may vary the block size to be searched. Large block sizes require more computation, but for certain image types (e.g. noisy data) large blocks will give a higher quality result (i.e. lower minimum SAD versus mean SAD)

2. The system adaptively changes the search area based on the previous motion estimate. If the last motion was 10 pixels to the right then the search may be over an area from 0 pixels to the right to 20 pixels to the right. i.e. the search area is centered on the expected motion as indicated by the previous motion measurement).

3. If the detected motions exhibit little variation (e.g. 7, 8, 10, 9 pixels to the right in successive motion measurements, as opposed to 5, 15, 8, 12 pixels) then the system may use a smaller search area since there is a relatively high degree of confidence that the motion will be between 7 and 10. Conversely, if successive motion estimates are widely varying, then the system preferably uses a larger search area in order to maximize assurance of a successful search (i.e. the motion is not beyond the limits of the search area). In the above example, if pixel motions are 7, 8, 10, 9 then we use a 15× 15 search area but if pixel motions are 5, 15, 8, 12 then we use a 30×30 search area.

4. Since most motion is expected in the lateral direction rather than in the range direction (because the transducer is drawn across the skin surface) the search area may be asymmetric. e.g. +/−5 pixels in range direction and +/−20 pixels in the lateral direction.

5. The search may be performed at multiple levels of spatial resolution. Initially, the search is made coarsely along the lateral direction only, e.g. test every second pixel location. Once the approximate lateral offset has been thus detected, a fine search (every pixel location) is made in both the lateral and range direction.

6. Hierarchical motion detection can be used based on multiple levels of signal level resolution. Initially, only the most significant 2 or 4 bits associated with each pixel intensity level are used to find the position with the minimum SAD. Once the location has been approximately found, a second level of search is performed in that region using all the bits, typically 8. More than two levels of hierarchy can be used.

Higher Resolution Tracking Techniques

The finest level of motion detection may be enhanced by interpolating additional pixels between the available pixels. An alternative method described by Li and Gonzales, *IEEE Trans on Circuits and Systems for Video Techn.*, 6, 1, pg. 118 (February, 1996), calculates the motion estimate to sub-pixel resolution based on the values of the neighboring SAD values to the one with the minimum SAD.

Techniques for Combining Motion Estimates

The final estimate of transducer motion is preferably based on a composite of multiple inputs. Preferably these inputs are weighted so that those that appear to possess the greatest quality (or certainty) are given the most weight. Inputs which are contradictory with the majority of inputs are either eliminated from the composite calculation or are given very small weightings.

Firstly the ratio of minimum sum of absolute differences ("min_SAD") to mean sum of absolute differences ("mean_SAD") is used as a quality factor. A low ratio indicates a high quality result and a result close to 1.0 indicates an unreliable estimate. In practice a good ratio is rarely less than 0.3. Assuming that ratios lie in the range 0.3 to 1.0, we can convert this into a weighting function in the range 0.0 to 1.0, where 1.0 means an ideal (high certainty) result and 0.0 means an unusable result:

Weighting_MSAD=(1−(min_SAD/mean_SAD))/0.7.

If the minimum observable SAD is <0.3, then this equation can be modified:

Weighting_MSAD=(1−(min_SAD/mean_SAD))/(1−min_observable_SAD).

A second quality factor is based on the similarity of the present motion estimate to the previous estimate. This approach is based on the observation that during a smooth scan typical of that which would be used in practice, the actual relative motion between one set of tracking data and a subsequent set of tracking data is similar. If a motion estimate predicts a reversal in motion, then it is probable that it is a bad estimate. Causes for bad estimates may include a noisy image, poor pixel contrast, or the presence of large amounts of flowing blood. Notice that the previous motion estimate that is used as a reference may be either the raw estimate of motion from the MSAD operation or the previous smoothed and weighted estimate. Preferably, the smoothed previous motion estimate is used as the reference to which the most recent raw motion estimate is compared.

In the current example the degree of similarity between two estimates of motion is calculated as follows. This example is for Y (elevation) direction motion, but it can be applied to Z (depth) direction motion. Weighting_seq is the weighting factor that is generated based on a comparison of sequential estimates.

Weighting_seq=1 − [abs (Ycurr-Ylast)/(abs (Ycur) + abs (Ylast))],
where Ycurr = the current estimate of Y motion, and
Ylast = the last estimate of Y motion, smoothed.

For the initial motion calculation, no measure of similarity to a previous estimate is possible, so the initial motion-related weighting must be given an arbitrary value such as 0.5.

A composite weighting factor ("Weighting_comp") is then formed. Depending on experience with real tissue scanning, one may select to bias the weighting more to either the MSAD quality or to the sequential quality. Currently 0.75 of the total weighting is related to the MSAD quality and 0.25 to the sequential quality.

Weighting_comp=0.75×Weighing_MSAD+0.25×Weighting_seq.

These weightings are calculated for all the points for which motion estimates were made. In an example 6 motion estimates were made in the range direction. Each used a 48×48 pixel block.

Since for a real motion the equation describing the motion as a function of depth must follow a straight line, we can fit the obtained motion estimates to a straight line. Preferably, the motions are fitted using a weighted least squares method wherein the weightings are those described above for each of the range points for which a motion estimate is available. This process is repeated for both Y direction motion and Z direction motion.

Finally, having determined the fitted motions, we have the line defined in terms of an intercept (c) and slope (m): Y_motion=mZ+c.

Similarly, the Z motions as a function of the Z observation points are calculated:

$$Z\_motion=mZ+c (\text{different } m \text{ and } c).$$

Although one would typically expect Z_motion to be a constant as a function of Z, it is not in the case of transducer rotation about the azimuthal axis.

This fitted value may be further smoothed based on the average of the parameter Weighting_comp. Hence, in the presence of a very poor quality estimate, the current estimate is based principally on the previous (rather than the current) estimate:

| | |
|---|---|
| m_mod = fact * (mean (Weighting_comp)) * m + (1-fact * (mean (Weighting_comp)) * m_last | |
| c_mod = fact * (mean (Weighting_comp)) * c + (1-fact * (mean (Weighting_comp)) * c_last | |
| c | the current estimate of intercept |
| c_last | the intercept from the previous pair-of-frames motion estimate |
| c_mod | the modified intercept |
| m | the current estimate of slope |
| m_last | the slope from the previous pair-of-frames motion estimate |
| m_mod | the modified slope |
| fact | a factor to determine how much significance to attach to the weighting (fact = 1.0 presently) |

Figure 34:
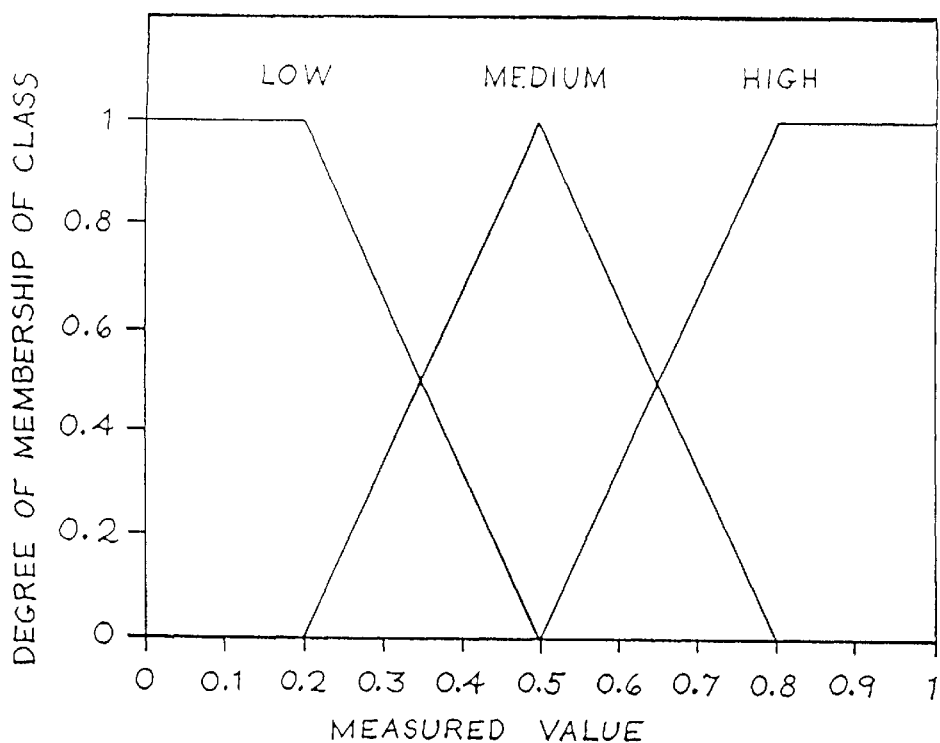
FIGS. 34 through 37 are graphs illustrating operation of a fuzzy logic system included in an alternative form of this invention.
Figure 35:
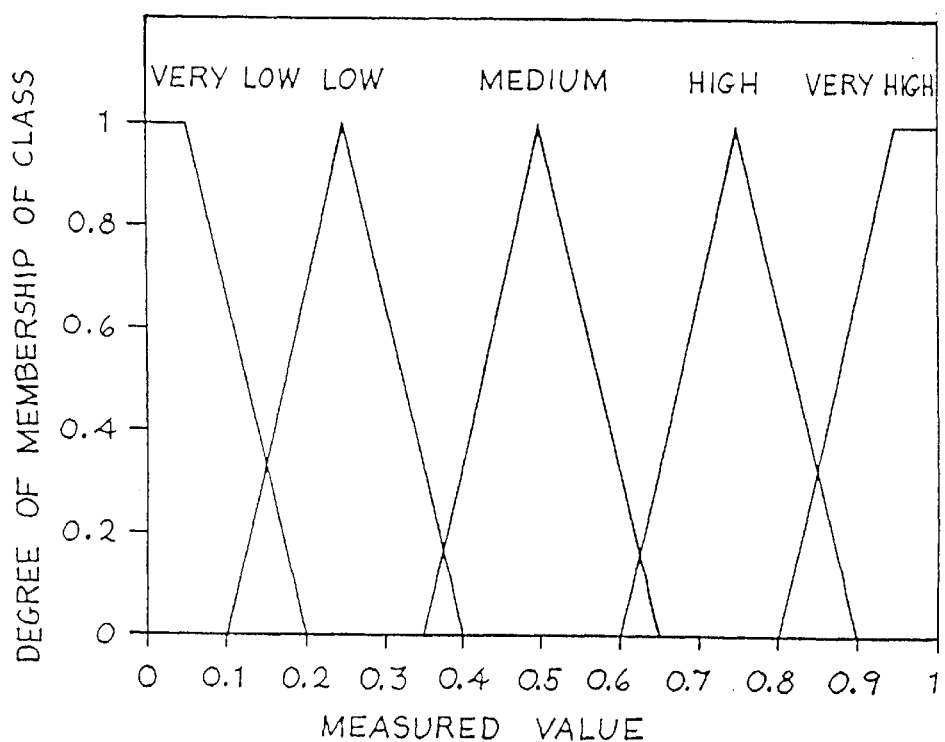

Alternatively, the final Weighting_comp may be determined using fuzzy logic. A fuzzy logic control block takes as inputs Weighting_MSAD and Weighting_seq and combines them to form an output which is Weighting_comp. Inputs Weighting_MSAD and Weighting_seq are first assigned to classes (separate classes for Weighting_MSAD and Weighting_seq). These classes are 'low', 'medium' and 'high'. Membership is based on whether the input comes within each of three triangular-like regions shown in FIG. 34. The derivation of positions of the lines defining in which classes particular measured values will reside is based on experimentation. Although the illustrated regions of the drawings are shown as triangular in shape, it should be noted that the regions may be shaped to follow any continuous function that is determined experimentally to give good results. The horizontal axis of the class function corresponds to the input value (Weighting_MSAD or Weighting_seq) and the vertical axis defines the degree of membership of the class. In this case, the same class membership diagram is used for both Weighting_MSAD and Weighting_seq. A similar class of membership diagram is derived for the fuzzy output Weighting_comp, as shown in FIG. 35. In this case the diagram has five regions—very low, low, medium, high and very high.

The following fuzzy rules can be applied to determine Weighting_comp; in these rules a logical AND is assumed between Weighting_MSAD and Weighting_seq:

| Rule No. | Weighting_MSAD | Weighting_seq | Weighting_comp |
|---|---|---|---|
| 1 | low | low | very low |
| 2 | low | medium | low |
| 3 | low | high | medium |
| 4 | medium | low | very low |
| 5 | medium | medium | medium |
| 6 | medium | high | high |
| 7 | high | low | low |
| 8 | high | medium | high |
| 9 | high | high | very high |

Fuzzy rules are applied to determine the truth of the rules. For example, assume that Weighting_MSAD and Weighting_seq are 0.35 and 0.9 respectively.

The 0.35 input results in 0.5 degree of class membership in 'Low' and 0.5 degree of class membership in 'Medium'. The 0.9 input results in 1.0 degree of class membership in 'High'.

Therefore Rules 3 and 6 are true but provide different values for the output Weighting_comp ('medium' and 'high' respectively). The outputs that are possible for these rules are shown in FIG. 36.

Referring firstly to Rule 3, the low value of Weighting_MSAD is combined with a logical AND with the high value of Weighting_seq and the minimum value of the two expressions is taken as the truth level of Rule 3. The 0.5 degree of membership of 'low' for Weighting_MSAD is less than the 1.0 degree of membership of class 'high' for Weighting_seq. Hence the truth level of the Rule 3 is 0.5.

Referring to Rule 6, the medium value of Weighting_MSAD is combined with a logical AND with the high value of Weighting_seq and the minimum value of the two expressions is taken as the truth level of Rule 6. The 0.5 degree of membership of 'medium' for Weighting_MSAD is less than the 1.0 degree of membership of class 'high' for Weighting_seq. Hence the truth level of the Rule 6 is 0.5.

Figure 36:
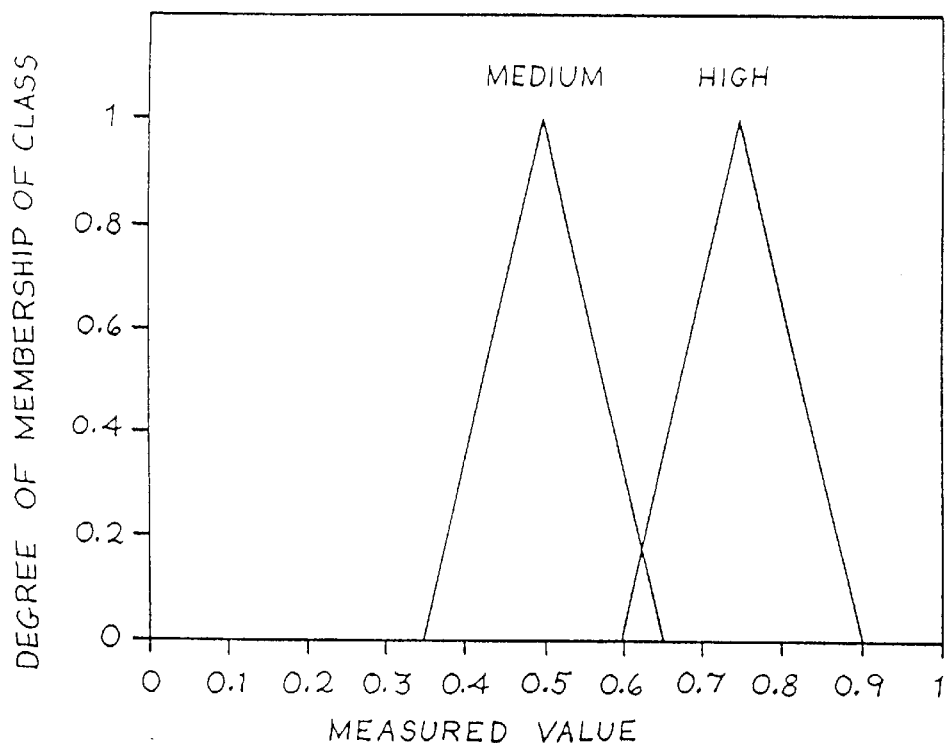
Figure 37:
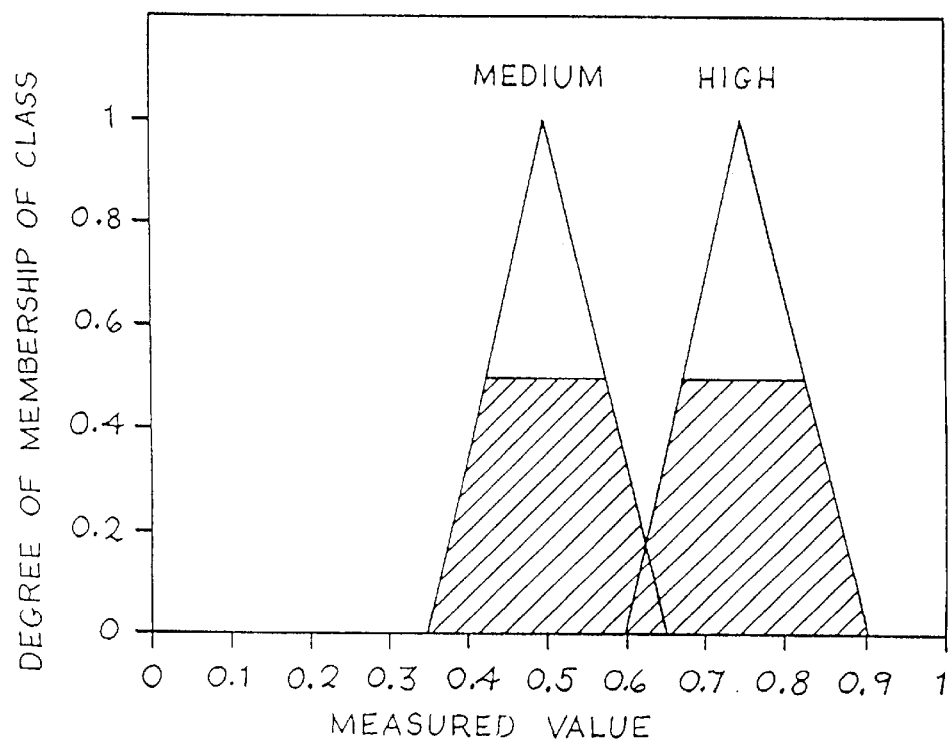

The 'medium' and 'high' labels for the Weighting_comp function membership in FIG. 36 are truncated at the truth levels defined by the fuzzy rules above. This is shown in FIG. 37.

A numerical output for Weighting_comp is derived using a centroid defuzzification technique. An estimate of the center of gravity of the entire shaded region in FIG. 37 is made. In this case, the center of gravity is at 0.625, and hence the output Weighting_comp is assigned this value.

Having determined Weighting_comp, one can use the method shown above to determine the weighted least squares fit and to determine to what extent the current motion should be based on the current motion estimate or on the previous motion estimate.

Of course, it will be apparent from the foregoing discussion that the detected motions in the X, Y and/or Z directions are local motions, i.e. motions with respect to the current position and orientation of the transducer and its arrays. Initially, at the start of the scan, it is typically assumed at the local X, Y and Z directions correspond to an assumed global axis system which remains constant throughout the motion of the transducer. If the transducer is rotated about the azimuthal axis of the image plane, as it might during a fan-like sweep, then the local Z motion (depth direction of the transducer) will rotate until it contains a significant component in the global Y or elevation direction. With every detected motion of the transducer, the new position and orientation of the transducer in the global axis system are calculated. The orientations of the local X, Y and Z directions (i.e. azimuth, elevation, and range or depth of the transducer) with respect to the global axis system are updated. Therefore, subsequent analysis of motion in the local Z direction of the transducer is decomposed into components in the global Z and Y directions, for example.

By way of example, consider the situation where the depth or Z direction of the transducer has been rotated from initially pointing down in alignment with the global Z direction to being angled at 45° with respect to the global Z direction. A motion in the local Z direction of the transducer of ten pixels is now decomposed into 10 cos (45°) in the global Z direction plus 10 cos (45°) in the global Y direction. In this example, the local Z direction is still orientated perpendicularly with respect to the global X direction, and hence a local Z motion has no component in the global X direction.

In general, the relation of the local axis directions with respect to the global axis directions can be calculated using cosines, which are continuously updated as the transducer is swept through the volume. Preferably, these direction cosines are maintained continuously for all three axes.

As used herein, the term "component of motion" is intended broadly to encompass translational components, rotational components, and combinations thereof.

Data Overlapping Techniques

When two regions of image data are combined to obtain an extended field of view as described above, a smooth interpolation scheme is preferably used at the boundaries of the data from different image data frames. As shown in FIG. 38, variable weighting factors can be used to provide such smooth interpolation schemes. In FIG. 38, the right-hand edge of the previous frame ends with pixel number 3 and the new portion of the frame begins with pixel number 4. The weighting factor used for the previous frame 1 varies from one within the old frame at pixels 0 and 1, smoothly down to 0 within the new portion of the frame at pixels 5, 6 and 7. Conversely, the weighting factor for the subsequent frame 2 varies from 0 within the old frame at pixels 0 and 1 gradually up to 1 for pixels 5, 6 and 7 of the new portion of the frame. In general, compounding can be used for accumulated image data in any of the embodiments described above to reduce noise in the image. Similarly, compounded data may be used with tracking data to reduce noise.

Techniques for the Detection of Incorrect Estimates of the Component of Motion

There are a variety of ways of using the motion estimates along the beam lines emanating from the tracking arrays to create a definition of the plane of the image array and the 3-D pixel locations for pixels on the image array plane.

One approach is to fit straight lines using a least squares or weighted least squares technique in which motion quality is used as a weighting factor. Based on these lines a number of points can be identified along with their associated 3-D motions. For example, four points can be selected at the top left, bottom left, bottom right and top right portions of the region, and bi-linear interpolation can be used to find pixel locations. From the motion estimates along the lines the equation for a plane (Y=a+bX+cZ) can be fitted. The quality of the fit may be measured by a least squares or weighted least squares technique. Then using the four key points identified previously, find the equation for a plane, i.e. fit three equations Y=a+bX+cZ for three points to find a, b, c using for example matrix inversion techniques. This step is repeated for a different set of three of the four key points. If the ratios a1/a2 (where a1 and a2 are the 'a' values derived from different sets of three points), b1/b2, or c1/c2 exceed a threshold (either too large or too small), the system can be programmed to warn the user via a video output that the plane is skewed, and that a rescan is appropriate.

The sum of squared errors, in either or both the line and plane case, may be used as a measure of low quality motion estimates and used either internally to adapt the motion estimate (i.e. use larger block sizes or make more motion estimates) or supplied to the user as a video or audible warning, as for example prompting a re-scan. Similarly, it is possible to accumulate the detected motion errors between successive motion estimates and to compare the cumulative motion error against a preset threshold. When the cumulative motion error crosses this threshold, the system is preferably programmed to warn the user that cumulative position error is unsatisfactory, and that a rescan is preferred. Optionally, the cumulative motion error (which may be derived from the sum of squared errors but is not necessarily exactly equal to the sum of squared errors) may be displayed for the user.

Alternative 3D Viewing Techniques

As described above, multiple 2D slices can be reconstructed into a solid 3D volume set. This is, of course, not the only approach that can be used to form the output display 46. For example, a simpler display may comprise a displayed reference bounding box which is 3D in form although displayed as a 2D projection. Using the motion detection information described above, the position and angular orientation of all of the planes of image data are calculated as before. However, in this alternative a selected 2D slice is displayed oriented within the 3D bounding box displayed on the screen. This can be done using the process described in Keller, U.S. Pat. No. 5,353,354. Techniques for projecting image data defined in 3 dimensions onto a 2-day screen are well known, as described for example in chapters 5 and 6 of *Computer Graphics* (Foley, et al., Addison-Wesley, 1995.) Of course, display of a single 2D slice within a 3D frame is a subset of the general 3D reconstruction and visualization system described above.

Alternative Beamforming Techniques

The embodiments described above use image data frames to collect data for display and tracking frames to collect data to determine relative motion of the transducers. Since the apertures for the image data frames and the tracking frames are physically separated, the collection of these frames of image data really form two independent beamformer tasks. If desired, multiple simultaneous transmit and/or receive beams can be used to reduce the time required to accumulate tracking data. One example of a multiple transmit-beam system, which could readily be adapted for simultaneously transmitting ultrasonic beams for the image data frames and the tracking frames is disclosed in U.S. patent application Ser. No. 08/673,410 now U.S. Pat. No. 5,675,554 issued Oct. 7, 1997, assigned to the assignee of the present invention. Similarly, a multiple receive-beam beamformer can be used to provide a separate receive beam for each transmit beam, thereby speeding data acquisition. The multiple receive-beam beamformer disclosed in U.S. patent application Ser. No. 08/432,615 now U.S. Pat. No. 5,685,308 issued Nov. 11, 1997, assigned to the assignee of the present invention, can be adapted for this purpose. See also the multiple receive-beam beamformer disclosed in O'Donnell U.S. Pat. No. 4,886,069.

The coherent image formation techniques disclosed in U.S. patent application Ser. No. 08/419,595 now U.S. Pat. No. 5,623,928 issued Apr. 29, 1997 and Ser. No. 08/418,640, now U.S. Pat. No. 5,667,373 issued Dec. 9, 1997, Wright et al., "Method and Apparatus for Coherent Image Formation" (assigned to the assignee of the present invention) can be used advantageously with selected embodiments of this invention. The system of the Wright patent applications provides phase alignment between adjacent scan lines in the near field, and, therefore, provides a shift-invariant speckle pattern. Such a shift-invariant speckle pattern should provide superior image motion detection based on the speckle tracking than that attainable with a conventional system in which the speckle pattern is shift variant due to a lack of phase alignment between scan lines.

Figure 41:
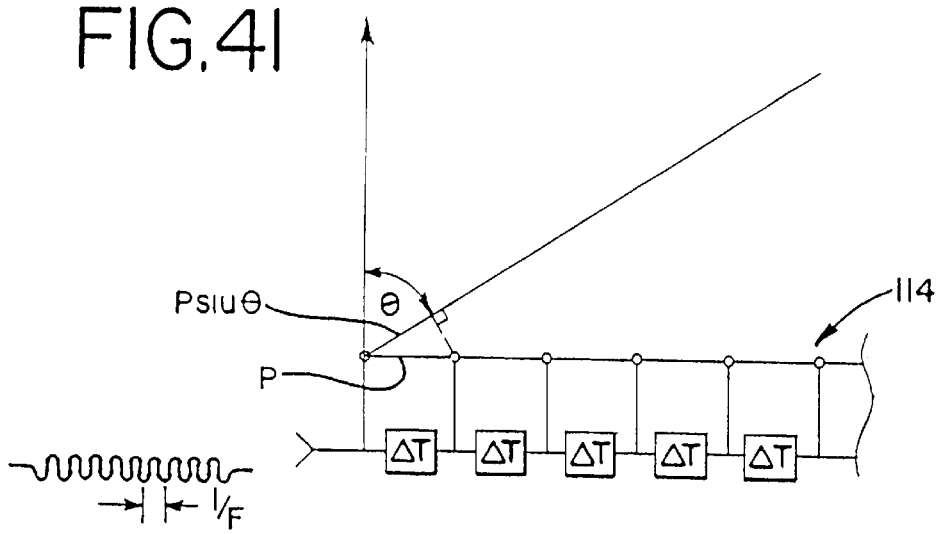
FIGS. 41 and 42 are schematic views of alternative systems for generating transmit signals.

Very low cost scanning is possible using a frequency sweep technique to perform an angular scan. Consider the system shown in FIG. 41, in which a tracking array is provided with a plurality of transducer elements separated by a pitch P. Each of the transducer elements is connected via time delay elements to an input signal. As shown in FIG. 41, in this case the input signal is a relatively narrow band pulse train comprising a tone burst 5 to 10 cycles in length having a fundamental period 1/F. Thus, transducer element n receives the input signal shown in FIG. 41 delayed by delay interval ΔT·n. The angle of the main lobe of the resulting beam is determined by the duration of the time delay ΔT and the period of the tone burst signal 1/F. By changing the frequency of excitation F, the angle of the scan line can be varied. Hence, for very little cost it is possible to scan the region. Of course, axial resolution of the resulting beam is not optimal, since for any given direction the signals are narrow band and hence have a long duration. In principle, it is possible to transmit with a broad band pulse, and then to use separate band pass filters for different frequencies so as to form multiple beams simultaneously. In the system of FIG. 41 constructive interference, and therefore the primary beam direction, is achieved when P·sin θ is equal to v/F where P, θ and F are as shown in FIG. 41 and v is the speed of sound in tissue. By sweeping the frequency of the input signal, and therefore the period 1/F, the resulting beam can be caused to sweep in angle θ.

Figure 42:
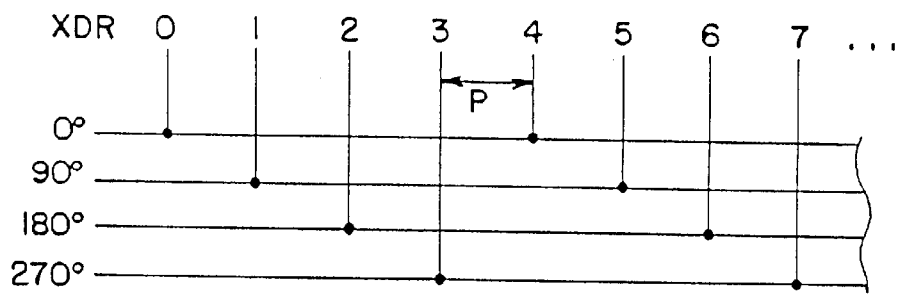

Another approach, as shown in FIG. 42, uses a set of mutually delayed signals, such as four signals in the example of FIG. 42. Each signal is a relatively narrow band tone burst., and in the example of FIG. 42 the various signals are delayed from one another by multiples of 90°. Typically, the length of the tone burst is related to the number of transducer elements and the times the signal is repeated across the array. For example, a 32 element array may use an eight cycle tone burst. As before, by varying the frequency of the input signal, the steering angle is varied. This approach is similar to that of FIG. 41, except that the four input signals are directly generated rather than time delayed with respect to one another in a progressive fashion as shown in FIG. 41. In this case, constructive interference occurs at the angle θ satisfying the following equation:

$$4P \cdot \sin \theta = (1/F) \cdot v,$$

where v is the speed of sound in the medium as discussed above.

In alternative embodiments three signals spaced at a mutual delay of 120° may be used instead of the four-signal arrangement described above. However, four delay signals are often preferred for reasons of availability of components for producing 90° phase shifts in sinusoidal signals. This approach provides adequate lateral resolution at a low cost.

According to the method described above, first an ultrasound transducer is provided comprising an imaging and a tracking array of any of the types described above. Then a transmit signal is provided to each element of the tracking array, this transmit signal having a plurality of cycles and a characteristic frequency. Then the frequency of the transmit signal is varied to control the scan direction. As pointed out above, the transmit signals may be progressively delayed versions of a single input signal or they may be directly generated.

Alternative Operator Warning Messages

If one of the tracking arrays detects motion but the other does not, this condition may be taken as an indication that the tracking array showing no motion is not in tissue contact. Preferably, the system controller includes programmed logic that responds to this condition by alerting the system operator with a warning message, such as an audible tone or a visual message on a display screen.

Figure 43:
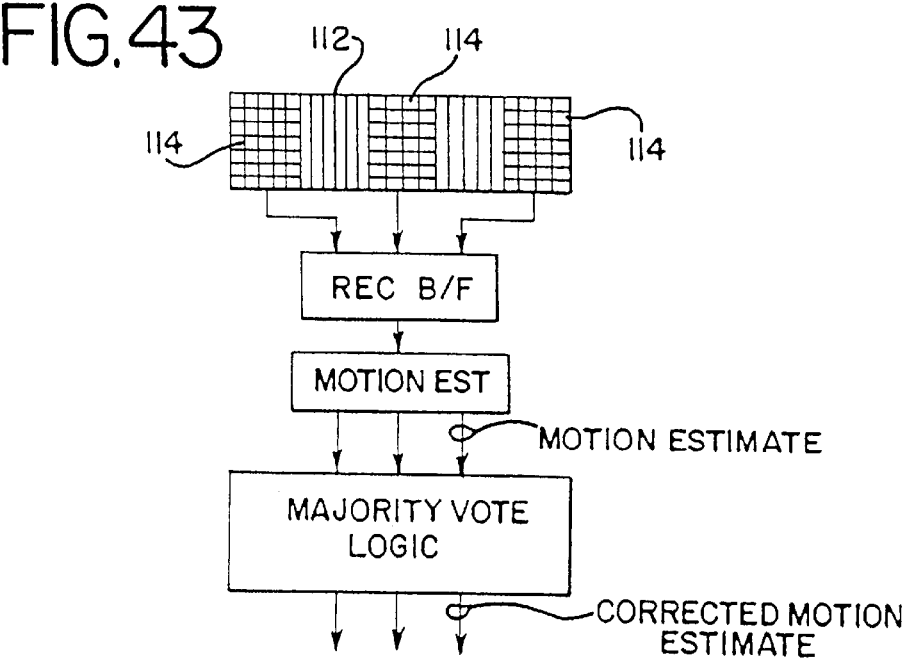
FIG. 43 is a schematic view of a system for detecting an erroneous motion estimate.

For example, as shown in FIG. 43, a transducer can include a single image data array 112 and three tracking arrays 114. Tracking data from the three tracking arrays 114 is processed by a receive beamformer to generate three sets of tracking images that are applied to a motion estimator. This motion estimator generates three motion estimates, each associated with a respective one of the tracking arrays 114. These three motion estimates are applied to a majority voting logic block, which compares the three estimates for a common point in time. It is anticipated that from time to time one of the tracking arrays may lose contact with the body of interest. Typically, one of the end arrays will lose contact first. If one of the tracking arrays produces a false motion estimate, because it is not in contact with tissue, the majority voting logic block determines the false motion estimate since it is in a minority. Alternatively, the quality of a motion estimate can be assessed by comparing the minimum sum of absolute differences to the mean some of absolute differences. Once an unreliable motion estimate has been isolated, a corrected motion estimate can be supplied which is extrapolated or interpolated from the motion estimates obtained with the remaining tracking arrays.

Single Block Motion Estimators

Although the overall motion between adjacent image frames can be estimated based on a collection of motion estimates in small regions as described above, it is also possible to estimate motion using a single large motion estimation block. When a collection of motion estimates is used, it is preferred to detect translation. A component of rotation may be inferred if the translations are not all similar. When a single block is used for motion detection, it is preferred to calculate both the components of translation and rotation directly from this block. In general, the axis of rotation between a reference frame and a subsequent frame may lie anywhere within the image plane or outside the image plane. Fortunately, modest errors in the location of the axis of rotation are tolerable, since, for example, a small rotation about an axis well outside the image frame causes a detected motion which is practically equivalent to a pure translation. If a single block is used for motion detection, then the following algorithm can be used:

1. Select a subset of the image frame pixels from a first or reference image frame. This subset is selected to ensure that the subsequent computations are manageable. If the reference frame is 400×300 pixels, then a block 160×160 pixels may be selected, centered at the center of the reference image frame.

2. Computational processing time limitations may make it preferable to use a smaller block such as a 40×40 or an 80×80 reference block for the motion estimate. In this case, the 160×160 pixel block is desampled after lowpass filtering to prevent aliasing.

Figure 39:
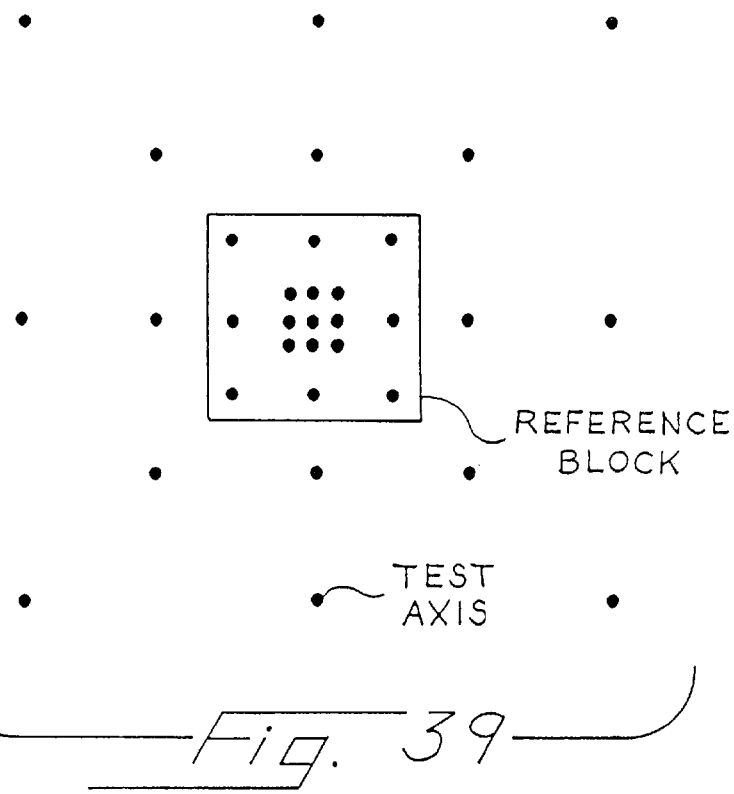
FIGS. 39 and 40 are schematic views that relate to a single block motion estimation system.

3. A matrix of test axes of rotation is then defined, as shown, for example, in attached FIG. 39. Preferably, the number of test axes is as large as possible, given the constraints of computation time. In some cases many more test axes than those shown in FIG. 39 can be used.

4. A correlation search is then performed. This search comprises taking the 80×80 reference block from the first frame and comparing it to the current frame and testing for the minimum sum of absolute differences assuming:

(a) Rotation of the test block or the current frame about each of the defined test axes;

(b) For each test axis, rotating through a predetermined set of rotations, for example, between −4° and +4° in two degree steps. When rotation is performed, it is preferred to interpolate pixel values in the rotated block (whether the reference or current block) so that the pixel values directly overlie one another.

(c) For each test axis of step (a) and for each rotation of step (b), the pixels in one of the two blocks being compared are translated in both the X and Y axes by up to ±10 pixels.

(d) For each test axis, each rotation, and each translation, the minimum sum of absolute differences is calculated between the reference block and the subsequent frame. The best correlation, as determined, for example, by the minimum sum of absolute differences, is then used to determine both the translation and the rotation of the subsequent frame with respect to the reference block.

Figure 40:
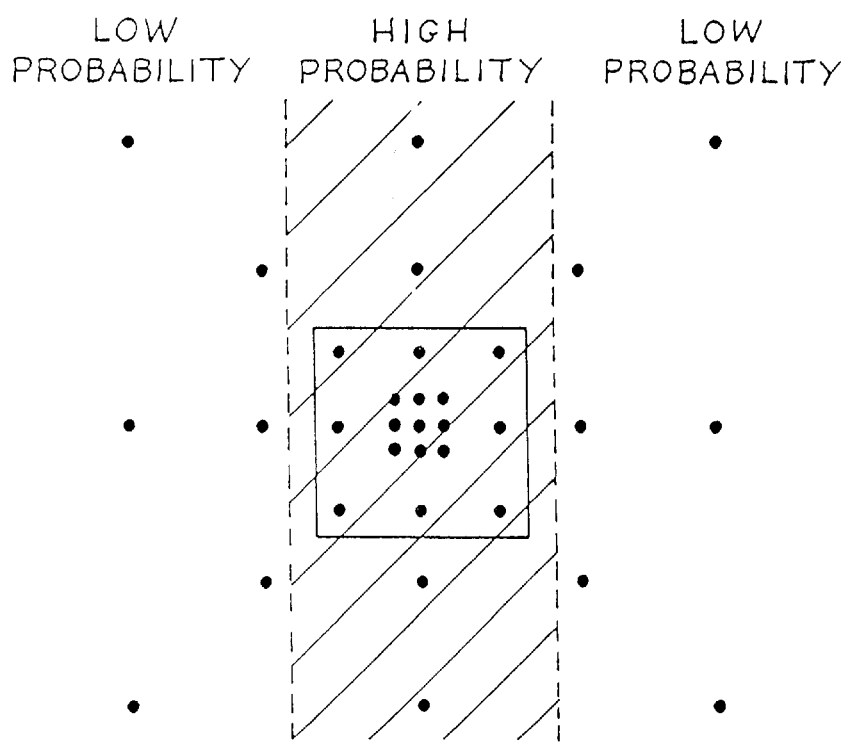

In this way, a single reference block can be used to determine both translation and rotation. Preferably, the search for the minimum sum of absolute differences uses the previous estimate of motion as a starting point for the search for the current estimate of motion. This approach reduces the total time required for the calculation. Experimentation can be used to determine the most efficient search in terms of the likely locations for the axis of rotation, the likely range of rotation between successive frames, and the likely range of translations between successive frames. As an example, it is most likely that the axis of rotation will lie in the region defined in FIG. 40, and it is most likely that rotation between successive frames will be small.

Any of the foregoing embodiments can be adapted to utilize a selectively received harmonic component for tracking, imaging, or both.

As is known in the art, harmonic imaging provides advantages in certain applications. In one form of harmonic imaging, ultrasonic energy concentrated near a fundamental frequency (such as 2 MHz for example) is transmitted into a target such as a tissue of a medical subject. Ultrasonic echo information from the tissue is selectively received such that a harmonic component of the echo information is processed. This harmonic component is concentrated near a harmonic of the fundamental frequency (such as the second harmonic, or 4 MHz in the foregoing example). Harmonic imaging has in the past been performed both with and without added non-linear contrast agent. When non-linear contrast agent is added, it often comprises micro-bubbles that are carried by blood, and that radiate echo information at the harmonic frequency. In tissue harmonic imaging, non-linear effects in the tissue distort a component of the transmitted acoustic signal, giving rise to harmonic (e.g., second harmonic) components not present in the transmitted signal.

It has been observed that tissue harmonic images as described above provide a particularly high spatial resolution and often possess improved contrast resolution characteristics. In particular, there is often less clutter in the near field. Additionally, because the transmit beam is generated using the fundamental frequency, the transmit beam profile is less distorted by a specific level of tissue-related phase aberration than would a transmit beam formed using signals transmitted directly at the second harmonic.

In order to enhance the harmonic image, it is preferred to shape the transmitted signal in the frequency domain such that substantially no harmonic energy is transmitted. This can be done using a suitably programmed transmit beamformer as described in U.S. patent application Ser. No. 08/771,345, filed Dec. 16, 1996 now U.S. Pat. No. 5,696,737 issued Dec. 9. 1997 and assigned to the assignee of the present invention, or a suitably filtered transmit beamformer as described in U.S. patent application Ser. No. 08/893,287, filed Jul. 15, 1997, and now U.S. Pat. No. 5,833,614 issued Nov. 11, 1998, Ser. No. 08/893,150 filed Jul. 15, 1997, and now U.S. Pat. No. 5,913,823 issued Jun. 22, 1999, and U.S. patent application Ser. No. 08/893,271 filed Jul. 15, 1997.

Many techniques are available for selectively receiving the harmonic component of the ultrasonic echo information. For example, a filter may be included in the receive signal processing path to block the transmitted fundamental component and to pass the desired harmonic component. This filter may be a time varying filter of the type described by Green, U.S. Pat. No. 4,016,750. Alternately a fixed, low pass filter may be used on a demodulated signal, wherein the demodulation carrier signal is selected to place the lower side band of the mixed signals such that what was the harmonic component in the RF domain now lies within the pass band of the fixed pass band or low pass filter. The mixed frequency may be at base band (centered at 0 Hz) or at some intermediate frequency (such as 2 MHz).

Harmonic imaging techniques can for example be used in the embodiment of FIG. 22. In this case, the transmit beamformer 15 produces shaped transmit signals for the transducer arrays 18, 20, 22. These shaped transmit signals concentrate the transmitted ultrasonic energy near the fundamental frequency $f_0$, while substantially blocking transmitted ultrasonic energy near the harmonic (e.g., $2f_0$).

Received signals from the transducer arrays 18, 10, 22 are filtered as explained above by the filter 13' included in the image data signal path and by the filter 13" in the tracking data signal path. The filters 13', 13" may be bandpass, low pass, or high pass filters.

In one embodiment the filter 13" is selected to pass the second harmonic component of the received signal and to block the fundamental component. Using the harmonic signal for the purpose of generating tracking information has the advantage that higher resolution and better contrast data is provided, and hence more accurate and reliable estimates of transducer motion are obtained. Tracking information may include modulated RF data or demodulated (e.g. I/Q) data, either before or after scan conversion. During tissue harmonic imaging, the target is maintained free of additional non-linear contrast agent throughout an entire medical ultrasound examination session that includes acquisition of the image data sets and the tracking data sets described above.

In another embodiment, the filter 13' is selected to pass the harmonic component and to block the fundamental component of the received signal such that the image data sets are created as a function of the harmonic component. By employing harmonic signals for generating image data sets a higher quality image is obtained for display, as for example in a 3-D volume image data set.

Many variations are possible. For example, it is possible to use the harmonic component in the near field and the fundamental component in the far field where penetration of the harmonic component is inadequate. This approach is discussed in detail in U.S. patent application Ser. No.

08/904,825 filed Aug. 2, 1997 (Attorney Docket 5050/227), assigned to the assignee of the present invention, and is applicable to both the image data sets and the tracking data sets. As another example, a combination of fundamental and harmonic components (e.g. average values) for either or both the tracking and image data is used. Additionally, the harmonic component of the received signal may be used for both the image data sets and the tracking data sets. In some cases, it is preferred to use harmonic components of different bandwidths for the two types of data sets; for example a narrower bandwidth may be used for tracking data and a wider bandwidth may be used for image data.

The harmonic component acquired by the image data array 18 may also be used for registering separate frames of image data to form an extended view, using the techniques described above. The harmonic component may be used either for the image tracking function or the image display function, depending upon the application. As an example, when the extended image includes data collected at a far-field range, it may be preferable to use the fundamental component of the received ultrasound information for the image data sets, since the fundamental component is characterized by a greater penetration depth. Since it is not necessary to perform image tracking at all depths (it may be adequate to calculate image motion in the near field only), it may be preferred to use the harmonic component for the image tracking function since the harmonic component has a higher spatial resolution and a higher contrast resolution and the comparison is being performed in the near field where penetration is not an issue. Other combinations of harmonic and fundamental components for the various combinations of tracking and image formation can be made, including the use of a combination (e.g. a sum) of fundamental and harmonic components for tracking or image formation.

As mentioned above, there is an advantage in making multiple motion estimates and accumulating these such that those with the greatest quality or certainty are emphasized. Multiple motion estimates may be made using fundamental and harmonic data and the results combined. In the very simplest case independently obtained motion estimates based on different frequency components of the received signal are simply averaged to obtain a final motion estimate.

Conclusion

The systems and methods described above provide a number of important advantages. They are insensitive to the electromagnetic environment and to patient motion, in contrast to magnetic orientation methods. The present invention is potentially implemented at lower cost than magnetic methods, and lower specification transducer arrays can be used. Potentially, the techniques described above can provide excellent accuracy of registration, since accuracy is determined by imaging resolution which scales with frequency.

Depending upon the application, the improved transducers described above may require more or larger cables, and the footprint of the transducer may be slightly extended. However, these potential problems may be minimized by using the techniques described above.

Of course, it is intended that the foregoing detailed description be regarded as an illustration of presently preferred forms of the invention, rather than as a limitation. It is the following claims, including all equivalents, which are intended to define the invention.

What is claimed is:

1. A method for forming an extended field of view of a target, said method comprising the following steps:
    (a) acquiring a plurality of sets of image information with an ultrasonic transducer array, said array moved substantially in an image plane between sets of image information, said image information representative of the target;
    (b) automatically determining rotational and translational components of motion in the image plane based on a plurality of comparisons of a single block of image information from a first one of said sets with a second one of said sets, said first and second ones of said sets acquired at different times; and
    (c) automatically using the components of motion determined in step (b) to register said first and second sets with respect to one another to form an extended field of view.

2. A method for forming an extended field of view of a target, said method comprising the following steps:
    (a) acquiring a plurality of sets of ultrasonic image information with an ultrasonic transducer array, said array moved substantially in an image plane between sets of image information;
    (b) automatically determining components of motion in the image plane based on a plurality of comparisons of a single block of image information from a first one of said sets of ultrasonic image information with a second one of said sets, said first and second ones of said sets acquired at different times; and
    (c) automatically using the components of motion determined in step (b) to register said first and second sets with respect to one another to form an extended field of view.

3. The method of claim 2 wherein steps (a)–(c) are performed during a medical ultrasound examination session, wherein step (a) comprises acquiring the ultrasonic image information at a harmonic of a fundamental transmit frequency and wherein the method comprises the further step of (d) maintaining the target free of additional non-linear contrast agent throughout the entire medical ultrasound examination session.

4. The method of claim 2 wherein the components of motion comprise rotational and translational components of motion.

5. A method for forming an extended field of view of a target, said method comprising the following steps:
    (a) acquiring a plurality of sets of image information with an ultrasonic transducer array, said array moved substantially in an image plane between sets of image information;
    (b) determining a component of motion in the image plane based on a comparison of image information from a first one of said sets with a second one of said sets;
    (c) indicating a sweep rate associated with step (a) to a user as a function of the component of motion;
    (d) registering said first and second sets as a function of the component of motion; and
    (e) forming an extended field of view image as a function of the registration of step (d).

6. The method of claim 5 wherein step (c) comprises a visual indication.

7. The method of claim 5 wherein step (c) comprises an audile indication.

8. A method for forming an extended field of view of a target, said method comprising the following steps:
    (a) acquiring a plurality of sets of image information with an ultrasonic transducer array, said array moved substantially in an image plane between sets of image information;

(b) interpolating first and second data associated with spatial locations between the image information for first and second ones of the sets of image information, respectively;

(c) determining a component of motion in the image plane based on a comparison of image information from the first one of said sets and associated first interpolated data with the second one of said sets and associated second interpolated data;

(d) registering said first and second sets as a function of the component of motion; and (e) forming an extended field of view image as a function of the registration of step (d).

9. The method of claim 2:

wherein step (a) comprises the step of transmitting ultrasonic energy concentrated near a fundamental frequency into a target;

wherein at least some of the sets of image information comprise a selectively received harmonic component of received ultrasonic echo information, said harmonic component concentrated near a harmonic of the fundamental frequency.

* * * * *

UNITED STATES PATENT AND TRADEMARK OFFICE
CERTIFICATE OF CORRECTION

PATENT NO. : 6,201,900 B1  Page 1 of 1
APPLICATION NO. : 09/340542
DATED : March 13, 2001
INVENTOR(S) : John A. Hossack et al.

It is certified that error appears in the above-identified patent and that said Letters Patent is hereby corrected as shown below:

On the Title Page

In column 1, item (75), delete "Samuel H. Maslak, Woodside; Edward A. Gardner, San Jose; Gregory L. Holley, Mountain view;".

Signed and Sealed this

Twenty-second Day of August, 2006

JON W. DUDAS
*Director of the United States Patent and Trademark Office*